(12) United States Patent
Gonzalez et al.

(10) Patent No.: US 11,103,685 B2
(45) Date of Patent: Aug. 31, 2021

(54) HOLLOW MICRONEEDLE ARRAYS

(71) Applicant: KINDEVA DRUG DELIVERY L.P., St. Paul, MN (US)

(72) Inventors: Bernard A. Gonzalez, St. Paul, MN (US); Scott A. Burton, Woodbury, MN (US); Jia Hu, Mounds View, MN (US); Chin-Yee Ng, Oakdale, MN (US); Ryan Patrick Simmers, Fargo, ND (US); Thomas J. Gilbert, St. Paul, MN (US); Sean M. Burke, St. Paul, MN (US); Robert A. Harkins, Savage, MN (US); Larry A. Schleif, Monticello, MN (US)

(73) Assignee: Kindeva Drug Delivery L.P., St. Paul, MN (US)

( * ) Notice: Subject to any disclaimer, the term of this patent is extended or adjusted under 35 U.S.C. 154(b) by 465 days.

(21) Appl. No.: 16/025,141

(22) Filed: Jul. 2, 2018

(65) Prior Publication Data
US 2018/0304063 A1 Oct. 25, 2018

Related U.S. Application Data

(62) Division of application No. 13/386,937, filed as application No. PCT/US2010/043414 on Jul. 27, 2010, now Pat. No. 10,010,706.
(Continued)

(51) Int. Cl.
| | |
|---|---|
| *A61M 37/00* | (2006.01) |
| *A61M 5/20* | (2006.01) |
| *A61M 5/142* | (2006.01) |
| *A61M 5/145* | (2006.01) |
| *A61M 5/158* | (2006.01) |

(Continued)

(52) U.S. Cl.
CPC ...... *A61M 37/0015* (2013.01); *A61M 5/2033* (2013.01); *A61M 5/1454* (2013.01); *A61M 5/14248* (2013.01); *A61M 5/158* (2013.01); *A61M 5/3015* (2013.01); *A61M 5/425* (2013.01); *A61M 2005/14252* (2013.01); *A61M 2005/14506* (2013.01); *A61M 2037/003* (2013.01);
(Continued)

(58) Field of Classification Search
CPC .... A61M 2037/0023; A61M 2037/003; A61M 5/2033; A61M 5/14248; A61M 5/1454; A61M 2005/14252; A61M 2005/14506; A61M 2037/0061; A61M 2005/1585; A61M 2005/206; A61M 37/0015; A61M 5/158; A61M 5/3015; A61M 5/425; A61M 2037/0046
See application file for complete search history.

(56) References Cited

U.S. PATENT DOCUMENTS

| | | |
|---|---|---|
| 4,755,173 A | 7/1988 | Konopka et al. |
| 5,176,662 A | 1/1993 | Bartholomew et al. |

(Continued)

FOREIGN PATENT DOCUMENTS

| | | |
|---|---|---|
| CA | 2 820 537 | 11/2004 |
| EP | 0 004 669 | 10/1979 |

(Continued)

*Primary Examiner* — Amber R Stiles
*Assistant Examiner* — Sarah Zagorin
(74) *Attorney, Agent, or Firm* — Mueting Raasch Group

(57) ABSTRACT

The present disclosure relates to apparatus, assemblies, combinations, and methods for infusing fluids by hollow microneedles.

14 Claims, 16 Drawing Sheets

Related U.S. Application Data

(60) Provisional application No. 61/230,347, filed on Jul. 31, 2009.

(51) Int. Cl.
*A61M 5/42* (2006.01)
*A61M 5/30* (2006.01)

(52) U.S. Cl.
CPC ............ *A61M 2037/0023* (2013.01); *A61M 2037/0046* (2013.01); *A61M 2037/0061* (2013.01)

(56) References Cited

U.S. PATENT DOCUMENTS

| | | | |
|---|---|---|---|
| 5,257,980 A | 11/1993 | Van Antwerp et al. | |
| 6,132,755 A | 10/2000 | Eicher et al. | |
| 6,689,100 B2 | 2/2004 | Connelly et al. | |
| 6,945,952 B2 | 9/2005 | Kwon | |
| 7,097,631 B2 | 8/2006 | Trautman et al. | |
| 7,131,960 B2 | 11/2006 | Trautman et al. | |
| 7,250,037 B2 | 7/2007 | Shermer et al. | |
| 7,252,651 B2 * | 8/2007 | Haider | A61M 5/2033 604/137 |
| 8,246,582 B2 | 8/2012 | Angel et al. | |
| 2003/0050602 A1 | 3/2003 | Pettis et al. | |
| 2003/0199823 A1 | 10/2003 | Bobroff et al. | |
| 2004/0024367 A1 | 2/2004 | Gilbert | |
| 2004/0108339 A1 | 6/2004 | Hansen et al. | |
| 2006/0095061 A1 | 5/2006 | Trautman et al. | |
| 2006/0229559 A1 | 10/2006 | Marano-Ford et al. | |
| 2007/0088348 A1 | 4/2007 | Kochamba | |
| 2007/0276329 A1 | 11/2007 | Mernoe | |
| 2008/0039805 A1 | 2/2008 | Frederickson et al. | |
| 2008/0195035 A1 | 8/2008 | Frederickson et al. | |
| 2008/0281273 A1 | 11/2008 | Angel et al. | |
| 2010/0222743 A1 | 9/2010 | Frederickson et al. | |
| 2012/0109066 A1 | 5/2012 | Chase et al. | |

FOREIGN PATENT DOCUMENTS

| | | |
|---|---|---|
| EP | 1 834 589 | 9/2007 |
| JP | 2007-236844 | 9/2007 |
| RU | 2 209 640 | 8/2003 |
| WO | WO 2004/024211 | 3/2004 |
| WO | WO 2004/032990 | 4/2004 |
| WO | WO 2005/123173 | 12/2005 |
| WO | WO 2007/002521 | 1/2007 |
| WO | WO 2007/002523 | 1/2007 |
| WO | WO 2010/059605 | 5/2010 |

* cited by examiner

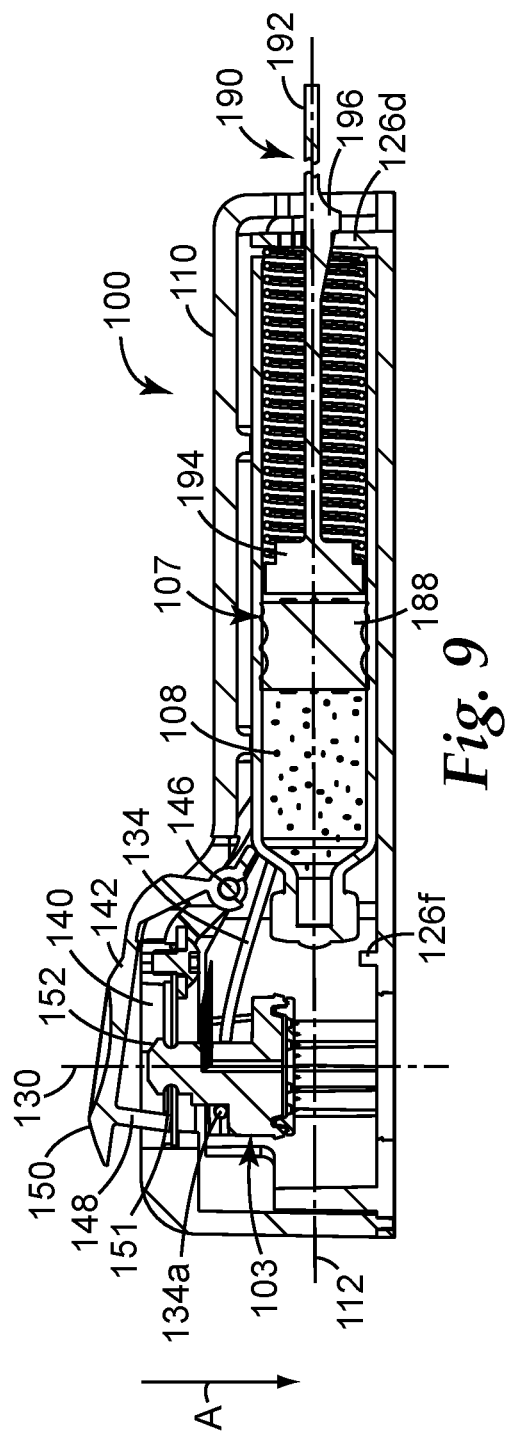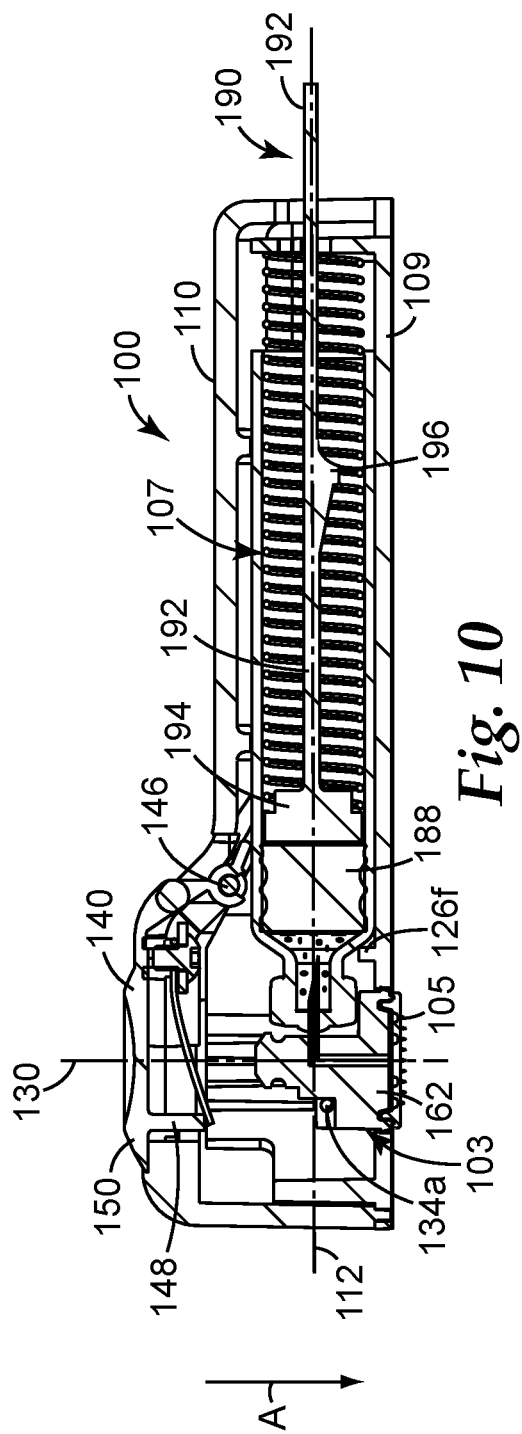

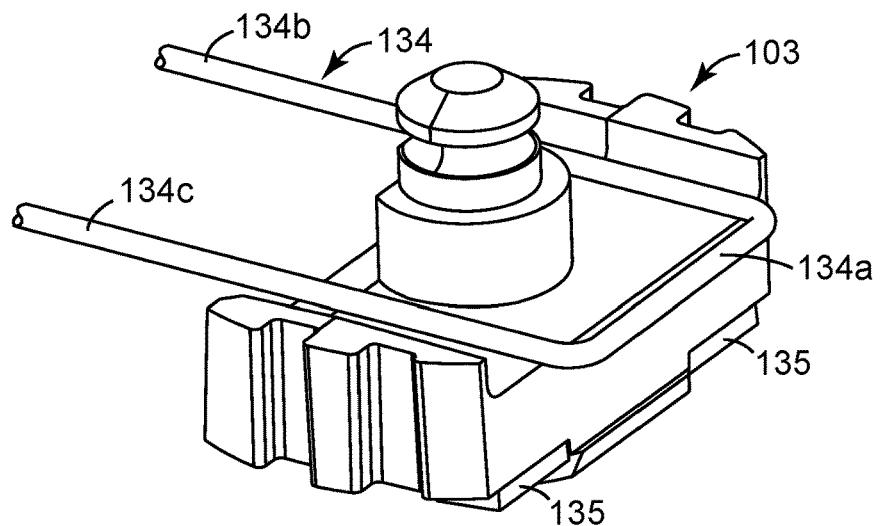
*Fig. 24*
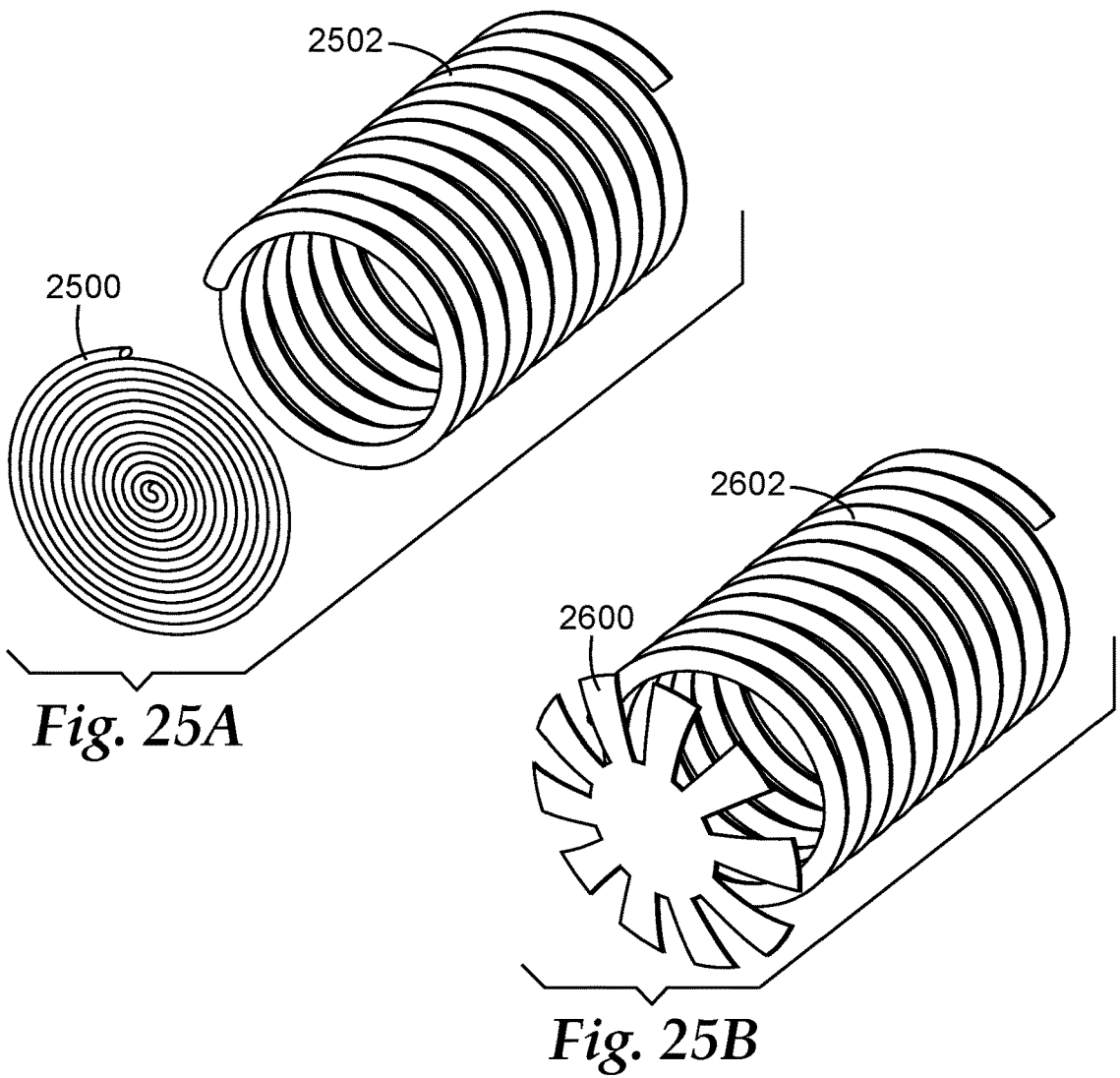
*Fig. 25A*
*Fig. 25B*

HOLLOW MICRONEEDLE ARRAYS

CROSS REFERENCE TO RELATED APPLICATIONS

This application is a division of U.S. patent application Ser. No. 13/386,937, filed Jan. 25, 2012, which is a national stage filing under 35 U.S.C. 371 of PCT/US2010/043414, filed Jul. 27, 2010, which claims the benefit of U.S. Provisional Patent Application No. 61/230,347, filed Jul. 31, 2009, the disclosures of which are incorporated by reference in their entirety herein.

SUMMARY

In one aspect, the present description is directed to an apparatus comprising a housing, a reservoir comprising a fluid and having an openable end, an applicator having a first major surface comprising a microneedle array, and a pathway communicable between the openable end and the microneedle array. The housing supports independently the applicator and the reservoir. The apparatus further comprises a first stored energy device actuatable for applying force to the applicator to accelerate the applicator in a direction generally normal to the first major surface and a second stored energy device actuatable for automatically opening the openable end, such that the openable end and the pathway are in fluid communication, and wherein the actuated second stored energy device forces the fluid through the openable end, the pathway, and the microneedle array.

In another aspect, the present description is directed to an apparatus comprising a housing, a reservoir storing a fluid and having an openable end, an applicator having a first major surface comprising a microneedle array, and a pathway communicable between the openable end and the microneedle array. The housing supports independently the applicator and the reservoir. The apparatus further comprises a first stored energy device actuatable for applying force to the applicator to accelerate the applicator in a direction generally normal to the first major surface. The apparatus also comprises a second stored energy device actuatable for automatically opening the openable end, such that the openable end and the pathway are in fluid communication, and wherein the actuated second stored energy device forces the fluid through the openable end, the pathway, and the microneedle array. Further, the housing includes an single actuator operably connected to both the first and second stored energy devices and being actuatable for actuating the first and second stored energy devices.

In yet another aspect, the present description relates to a method comprising providing a housing supporting (a) a drug cartridge, wherein the drug cartridge comprises a fluid and has an openable end, and (b) an applicator having a first major surface comprising a microneedle array. The method further comprises automatically displacing the microneedle array in a direction perpendicular to the first major surface, automatically opening the openable end, establishing fluid communication between the openable end and the microneedle array, and automatically forcing fluid from the drug cartridge into the microneedle array through the openable end.

BRIEF DESCRIPTION OF THE DRAWINGS

FIG. 9 is a longitudinal cross-sectional view of an apparatus according to the present description in a primed but inoperative condition.

FIG. 10 is a longitudinal cross-sectional view of the apparatus in an operative condition.

FIG. 24 is an enlarged view illustrating a shock absorber arrangement according to one exemplary embodiment of the present description.

FIG. 25A is a schematic view of one exemplary embodiment of a pair of spring devices.

FIG. 25B is a schematic view of another exemplary embodiment of a pair of spring devices.

DETAILED DESCRIPTION

Figure 1:
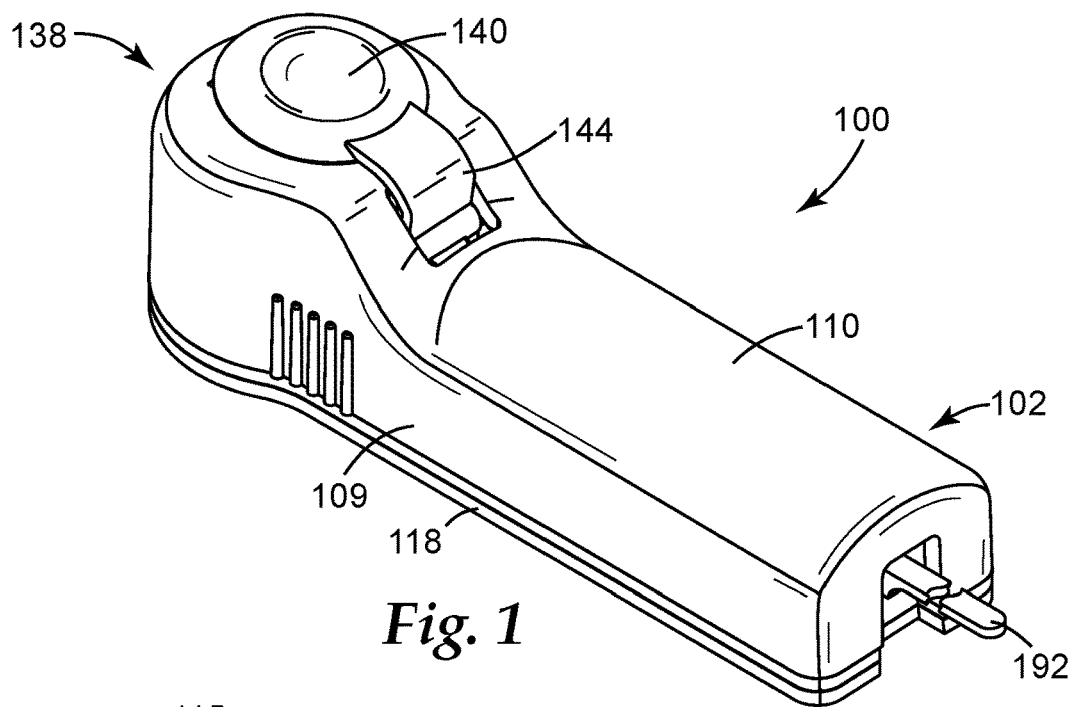
FIG. 1 is a perspective view of one exemplary embodiment of an apparatus of the present description.

The apparatus of the present description includes embodiments that may be activated by a single actuation to automatically and reliably penetrate a patient's skin by a microneedle array, for instance a hollow microneedle array, and then automatically release and dispense thereto a stored fluid from a reservoir (e.g., a ready-to-use drug cartridge) in a controlled manner that ensures consistent uptake. Advantageously, customizable and efficacious delivery of a wide variety of fluids and dosages to individual patients may be achieved in a relatively trauma free manner, while at the same time minimizing any likelihood of the hollow microneedles becoming dislodged during penetration and excess fluid remaining in the apparatus following dispensing.

The controlled fluid release apparatus 100 comprises housing 102, applicator 103 connected to microneedle array 104 carrying one or more hollow microneedles 105, and a fluid storage and delivery system 106 including reservoir 107 (which, in some embodiments, may be a drug cartridge). Advantageously, controlled fluid release apparatus 100 enables reservoir 107 to be installed by manufacturers, assemblers, or users. In addition, controlled fluid release apparatus 100 enables reservoir 107 and hollow microneedles 105 to be replaced, thereby permitting reuse. In addition, the reservoirs may be more easily cleaned, sterilized, filled, and refilled as compared to microneedle devices having fixed or dedicated drug reservoirs integral therewith.

The controlled fluid release apparatus 100 is adaptable to be "worn" by a patient during infusion/injection of fluid 108 (see, e.g., FIGS. 9, 10 & 13A-13C). In these exemplary embodiments, the controlled fluid release apparatus 100 may be directly applied to a patient's skin (See, e.g., FIG. 12) to accommodate ambulatory movement while keeping hollow microneedles 105 at an appropriate penetration depth(s).

As used herein, "hollow microneedle" refers to a specific microscopic structure that is designed for piercing the stratum corneum to facilitate the delivery of drugs through the skin. By way of example, microneedles can include needle or needle-like structures, as well as other structures capable of piercing the stratum corneum and delivering fluid.

Any substance that can be formulated in a fluid and delivered via hypodermic injection may be used, including any pharmaceutical, nutraceutical, cosmeceutical, diagnostic, and therapeutic agents (collectively referred to herein as "drug" for convenience). Examples of drugs that may be useful with the present invention include but are not limited to ACTH (e.g., corticotropin injection), luteinizing hormone-releasing hormone (e.g., Gonadorelin Hydrochloride), growth hormone-releasing hormone (e.g., Sermorelin Acetate), cholecystokinin (Sincalide), parathyroid hormone and fragments thereof (e.g., Teriparatide Acetate), thyroid releasing hormone and analogs thereof (e.g., protirelin), secretin and the like, Alpha-1 anti-trypsin, Anti-Angiogenesis agents, Antisense, butorphanol, Calcitonin and analogs, Ceredase, COX-II inhibitors, dermatological agents, dihydroergotamine, Dopamine agonists and antagonists, Enkephalins and other opioid peptides, Epidermal growth factors, Erythropoietin and analogs, Follicle stimulating hormone, G-CSF, Glucagon, GM-CSF, granisetron, Growth hormone and analogs (including growth hormone releasing hormone), Growth hormone antagonists, Hirudin and Hirudin analogs such as Hirulog, IgE suppressors, Insulin, insulinotropin and analogs, Insulin-like growth factors, Interferons, Interleukins, Luteinizing hormone, Luteinizing hormone releasing hormone and analogs, Heparins, Low molecular weight heparins and other natural, modified, or synthetic glycoaminoglycans, M-CSF, metoclopramide, Midazolam, Monoclonal antibodies, Peglyated antibodies, Pegylated proteins or any proteins modified with hydrophilic or hydrophobic polymers or additional functional groups, Fusion proteins, Single chain antibody fragments or the same with any combination of attached proteins, macromolecules, or additional functional groups thereof, Narcotic analgesics, nicotine, Non-steroid anti-inflammatory agents, Oligosaccharides, ondansetron, Parathyroid hormone and analogs, Parathyroid hormone antagonists, Prostaglandin antagonists, Prostaglandins, Recombinant soluble receptors, scopolamine, Serotonin agonists and antagonists, Sildenafil, Terbutaline, Thrombolytics, Tissue plasminogen activators, TNF-, and TNF-antagonist, the vaccines, with or without carriers/adjuvants, including prophylactics and therapeutic antigens (including but not limited to subunit protein, peptide and polysaccharide, polysaccharide conjugates, toxoids, genetic based vaccines, live attenuated, reassortant, inactivated, whole cells, viral and bacterial vectors) in connection with, addiction, arthritis, cholera, cocaine addiction, diphtheria, tetanus, HIB, Lyme disease, meningococcus, measles, mumps, rubella, varicella, yellow fever, Respiratory syncytial virus, tick borne Japanese encephalitis, pneumococcus, streptococcus, typhoid, influenza, hepatitis, including hepatitis A, B, C and E, otitis media, rabies, polio, HIV, parainfluenza, rotavirus, Epstein Barr Virsu, CMV, chlamydia, non-typeable haemophilus, *Moraxella catarrhalis*, human papilloma virus, tuberculosis including BCG, gonorrhoea, asthma, atherosclerosis malaria, *E-coli*, Alzheimer's Disease, *H. Pylori, salmonella*, diabetes, cancer, herpes simplex, human papilloma and the like other substances including all of the major therapeutics such as agents for the common cold, Anti-addiction, anti-allergy, anti-emetics, anti-obesity, antiosteoporeteic, anti-infectives, analgesics, anesthetics, anorexics, antiarthritics, antiasthmatic agents, anticonvulsants, anti-depressants, antidiabetic agents, antihistamines, anti-inflammatory agents, antimigraine preparations, antimotion sickness preparations, antinauseants, antineoplastics, antiparkinsonism drugs, antipruritics, antipsychotics, antipyretics, anticholinergics, benzodiazepine antagonists, vasodilators, including general, coronary, peripheral and cerebral, bone stimulating agents, central nervous system stimulants, hormones, hypnotics, immunosuppressives, muscle relaxants, parasympatholytics, parasympathomimetrics, prostaglandins, proteins, peptides, polypeptides and other macromolecules, psychostimulants, sedatives, and sexual hypofunction and tranquilizers. The present description envisions that even a gaseous fluid may be utilized.

Housing 102 may be self-contained and compactly constructed to provide a relatively low profile and small footprint for, among other factors, ease of use and patient comfort. In the illustrated embodiment of FIGS. 1 and 2, housing 102 may include lower housing portion 109 and mating upper housing portion 110 that provides a cover.

Figure 2:
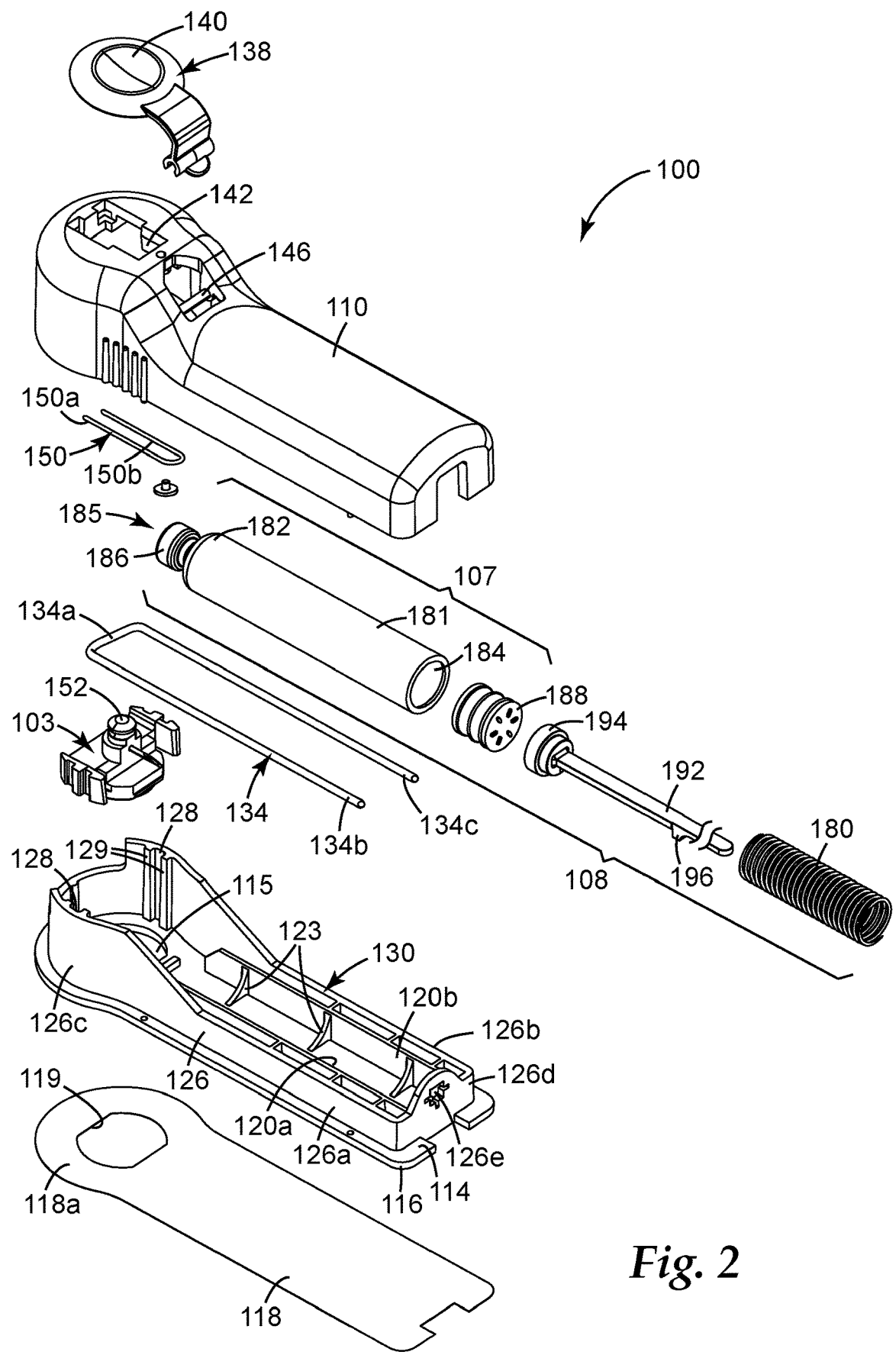
FIG. 2 is an exploded perspective view of the apparatus illustrated in FIG. 1.
Figure 5:
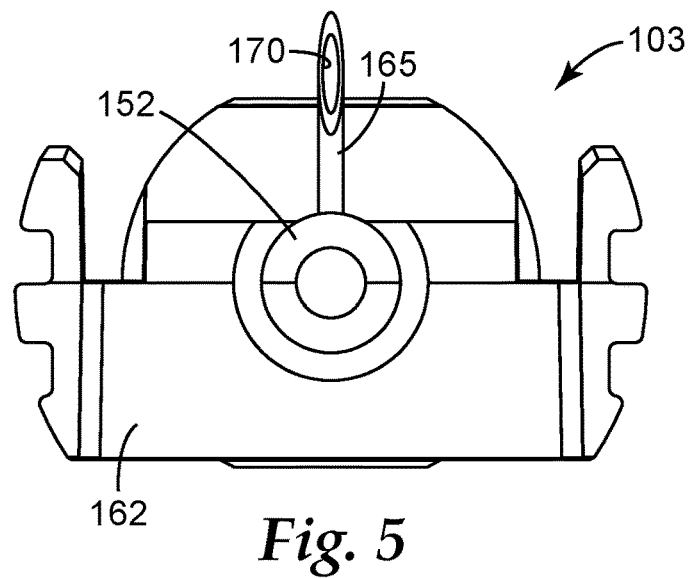
FIG. 5 is a plan view of one exemplary embodiment of an applicator used in the apparatus of FIG. 1.

Lower and upper housing portions 109 and 110 may be secured together by any suitable means including, but not limited to, snap-fit together or coupled by hinges, pivots, frictional interference fits, fasteners, and the like. For example, lower and upper housing portions 109 and 110 may be connected together by a hinge (not shown) that allows pivoting of clamshell like lower and upper housing portions. Housing 102 may be made of suitable lightweight materials compatible for delivering fluids of the kind noted above. The materials of housing 102 may include, but are not limited to, plastics, metals, composite materials, and combinations thereof. Lower housing portion 109 may include base 114 (FIG. 2), which may be generally planar, defining opening 115 for allowing hollow microneedles 105 to be displaced by first stored energy device 134. Base member 114 defines a relatively large and generally planar surface, first major surface 116 (FIG. 2). In some embodiments, base 114 is sufficient to support the controlled fluid release apparatus 100 in a comfortable manner when worn.

Adhesive layer 118 may be joined to all or part(s) of first major surface 116. Adhesive layer 118 (e.g., FIG. 2) may be any suitable type for the purposes described herein and may comprise, in one embodiment, a pressure sensitive adhesive covered by a release layer (not shown), the release layer could be removed prior to application of the pressure sensitive adhesive layer on the patient. Adhesive layer 118 is illustrated as being generally coextensive to first major surface 116. The present illustrated embodiment, also contemplates that adhesive layer 118 may be located immediately adjacent opening 115.

Many suitable pressure sensitive adhesives may be used in adhesive layer 118, such as, but not limited to, polyacrylates, polyisobutylenes, and polysiloxanes.

Adhesive layer 118 may also include annular portion 118*a* surrounding aperture 119 (e.g., FIG. 2). Aperture 119 may be in registry with opening 115 in lower housing portion 109. Annular portion 118*a* may have higher strength adhesive qualities than the remaining portion of adhesive layer 118 to ensure an even more secure coupling to the skin in the area surrounding needle penetration. It will be appreciated that variations may be made to the formulations of adhesive layer 118 for varying the strength of the adhesive securing the controlled fluid release apparatus to a patient's skin as well as other bodily tissues.

Continued reference is made to FIG. 2 wherein there is illustrated retaining wall assembly 120 which is upstanding from base 114 and is spaced laterally from the edges thereof. Retaining wall assembly 120 may include a pair of generally upstanding and spaced apart retaining wall portions 122*a* and 122*b* having curved ribs 123 for retaining and guiding reservoir 107 along longitudinal axis 107*a* (e.g., FIG. 12). Retaining wall portions 122*a* and 122*b* are disposed inwardly of laterally disposed and upstanding external wall 126 that includes lateral wall portions 126*a* and 126*b* generally parallel to retaining wall portions 122*a* and 122*b*. External wall 126 may include rounded portion 126*c* and rear wall portion 126*d*. Integrally molded to rounded portion 126*c* may be a pair of diametrically opposed inwardly facing channel portions 128 defined by respective ribs 129 facing inwardly. External wall 126 may include rear wall portion 126*d* having wall opening 126*e*.

Channel portions 128 retain and guide applicator 103 for displacement along a path generally perpendicular to first major surface 116, indicated by arrow A in FIGS. 9 and 10. Vertical axis 130 is generally normal to that of the longitudinal axis 107*a*. While in one exemplary embodiment, the motion of applicator 103 may be at substantially 90 degrees with respect to first major surface 116, it will be appreciated that the generally normal path may deviate from 90 degrees to assume orientations that can penetrate deep enough to deliver an intended dosage. Such paths generally ensure positive penetration to a targeted intradermal depth. As such, consistent uptake and efficacious administering of the fluids are enhanced.

Figure 29:
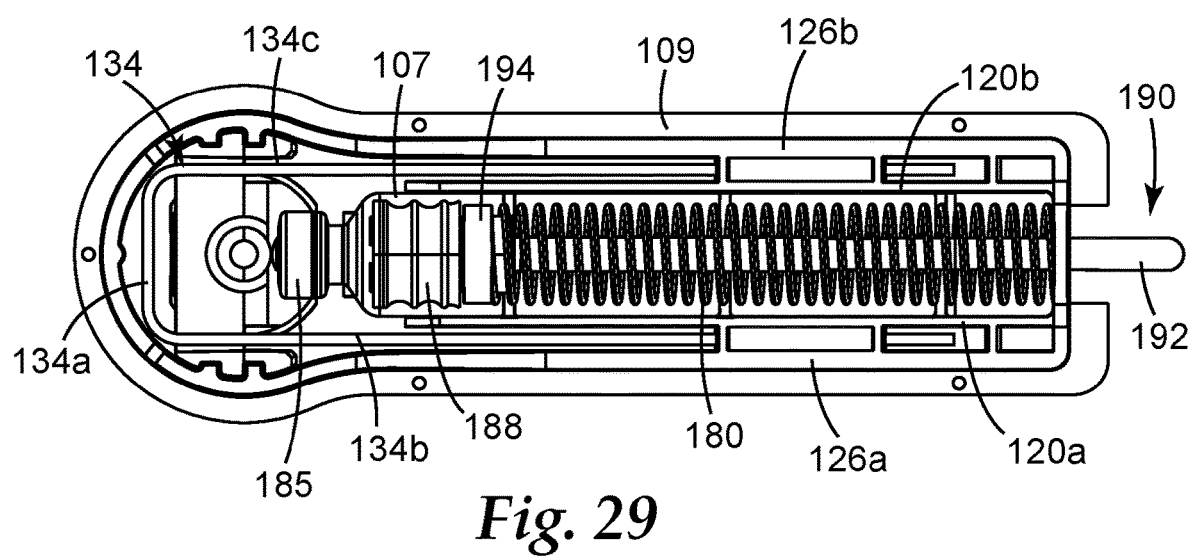
FIG. 29 is a plan view of the interior of a bottom portion of the housing of the apparatus illustrated in FIG. 2.

Controlled fluid release apparatus 100, illustrated for example in FIGS. 2, 9, and 29, depicts first stored energy device 134 that is actuatable for applying force to applicator 103 in a direction general normal to the first major surface. In some embodiments, such actuated force allows for movement of applicator 103 in a controlled manner, thereby ensuring application of the necessary forces for hollow microneedles 105 to penetrate the skin of a patient.

The Applicants have found that prior application devices may suffer from the shortcoming that users pushing down on microneedle dispensing devices (not shown) may use too much force or too little force, thereby resulting in unwanted variations in penetration force and depth. In some aspects, the presently described controlled fluid release apparatus overcomes this shortcoming of other devices.

In one embodiment, first stored energy device 134 may be a leaf-like spring arranged to apply to applicator 103 a controlled force, ensuring a consistent penetration to a targeted depth range. In the exemplary embodiment, as illustrated in, for example, FIGS. 12, 24 and 29, first stored energy device 134 may be comprised of a generally U-shaped leaf-like spring. Bight portion 134*a* of first stored energy device 134 rests on or may be otherwise coupled or supported directly on applicator 103.

As illustrated in FIG. 29, first stored energy device 134 may include leg portions 134*b*, 134*c* that are disposed between spaced apart retaining wall portions 122*a* and 122*b* and lateral wall portions 126*a* and 126*b*. Advantageously, such positioning of first stored energy device 134 within housing 102 immediately adjacent reservoir 107 not only simplifies construction and assembly of controlled fluid release apparatus 100, but also makes for a smaller footprint and lower profile, thereby significantly improving the overall construction.

In one exemplary embodiment, for example, first stored energy device 134 may be 7.5 cm×0.0625" (0.159 cm) outside diameter stainless steel spring. The present disclosure contemplates a variety of similar springs and spring constructions that may be used.

As noted above, the present inventors recognized a tendency for the microneedle applicators to recoil following impact against the skin due to factors that include the springiness of first stored energy device 134 and the elasticity of skin. It is also generally advantageous that hollow microneedles 105 penetrate to a predetermined depth in the dermis and remain at that depth (or within a certain depth range) during infusion. Some embodiments of the present description have the effect of dampening this recoil, thereby providing more precise delivery of the microneedle arrays described herein.

In one exemplary embodiment, first stored energy device 134 is not fixed to applicator 103. As such, following impact, first stored energy device 134 may freely recoil upwardly and vibrate without partially or totally withdrawing or lifting hollow microneedles 105 from the skin and their intended penetration depths. As such, the potential for leakage of the fluid to the surface of the skin occurring may be reduced, minimized or even eliminated. Alternatively, first stored energy device 134 may be made to maintain a positive pressure on applicator 103 throughout the skin impact and penetration, thereby avoiding potential partial or even total withdrawal of the microneedles.

It will be appreciated that the magnitude and frequency of spring recoil and vibration is directly related to primary factors such as the spring's free length, mass and material properties, and any tension or preload. Other factors may include the spring's shape and configuration, such as a multi-element stacked leaf-like spring, as in a stacked flat leaf spring arrangement; single straight length as in a single piece of round spring tempered wire; shaped wire-formed U-shaped, etc. Furthermore, first stored energy device 134 may be made with any cross-section, including, but not limited to, round, square, rectangular, any regular polygon, irregular in shape or even varying along its length. Such shape profiles may thereby confer stiffness and rigidity at portions where needed.

First stored energy device materials may include a carbon steel (e.g., music wire), oil tempered based alloys (e.g., beryllium copper, phosphor bronze), or other suitable alloys (e.g., Elgiloy™ cobalt alloy commercially available from Elgin Specialty Metals, Elgin, Ill., USA). While in the present exemplary embodiment, a metallic spring may be used that has a relatively high spring energy constant for sake of compactness, it is also possible that a less compact, non-metallic (e.g., plastic) spring element may be utilized, such as where the spring element is primed and fired within a short time frame.

First stored energy device 134 is actuatable for applying force to applicator 103 carrying hollow microneedles 105, typically at a velocity before impact ranging from between about 2 and about 20 m/sec before applicator 103 impacts a patient's skin. More typically, hollow microneedles 105 strike a patient's skin at a velocity before impact ranging from between about 4 and about 12 m/sec.

Reference is made to FIG. 24, illustrating another exemplary approach for avoiding recoil, potentially leading to partial or even total withdrawal of the microneedles, as discussed above. As illustrated, first stored energy device 134 rests on an upper or top surface of applicator 103 and compliant shock-absorbing assembly 135 is coupled to a lower or bottom surface of applicator 103 to reduce vibrations that might negatively affect the intended penetration of hollow microneedles. A wide variety of shock-absorbing materials may be used for compliant shock-absorbing assembly 135. These materials may include, but are not limited to, closed-cell and open-cell foam, elastomers or other energy dissipative elements that would absorb and dissipate the resulting recoil and vibration following impact of the microneedles.

In one exemplary embodiment, compliant shock-absorbing assembly 135 may comprise a pair of independent resilient pads that may be made from a variety of suitable materials that may include, but not be limited to silicone foam, visco-elastic foams, and solid silicone rubber. These resilient materials may have suitable thickness to accomplish the intended shock absorption. Exemplary thickness may range from about 0.1 mm to 3 mm and, more typically, from about 0.5 mm to about 1.5 mm.

In the exemplary embodiment, the shock absorbing material may be mounted on lower housing portion 109 (not shown) to be positioned to be engaged by the bottom of applicator 103. Alternatively or additionally, the resilient pads may be added to the upper surface of applicator 103 to be engaged by first stored energy device 134.

Reference is made now to FIGS. 1, 2, 4, and 8. The upper housing portion 110 may have a construction, such as illustrated, to envelop and cooperate with the lower housing portion 109 as noted. Upper housing portion 110 may be made of a single-piece, shell-like construction that is sized and shaped to generally match lower housing portion 109 for mating therewith. In the illustrated exemplary embodiment, upper housing portion 110 may also be made of a plastic, such as polycarbonate, acrylic and other similar materials. Upper housing portion 110 may also be transparent to allow a user to visually inspect the extent of the infusion. Alternatively, upper housing portion 110 may have a window (not shown) that similarly allows a user to easily visually observe the extent of the fluid being dispensed as well as piston displacement as will be described. This is particularly advantageous in situations involving infusions occurring over relatively long periods of time.

Figure 8:
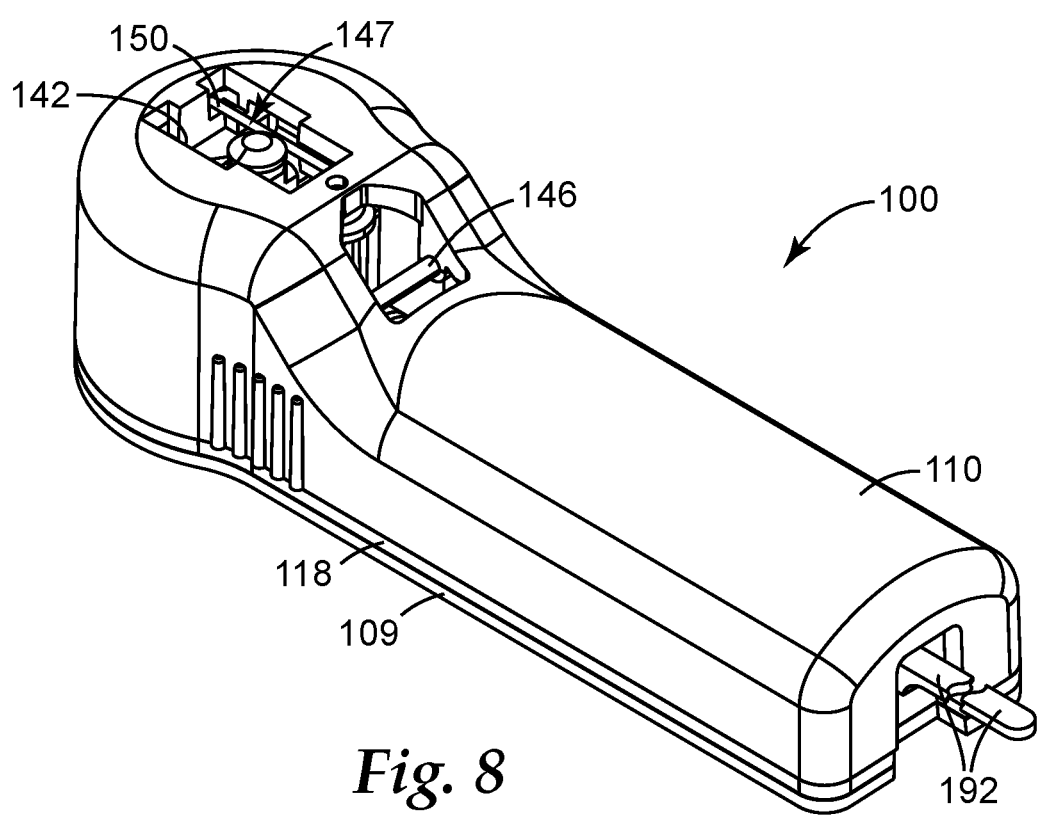
FIG. 8 is a perspective view similar to FIG. 1, with a cover removed.
Figure 11:
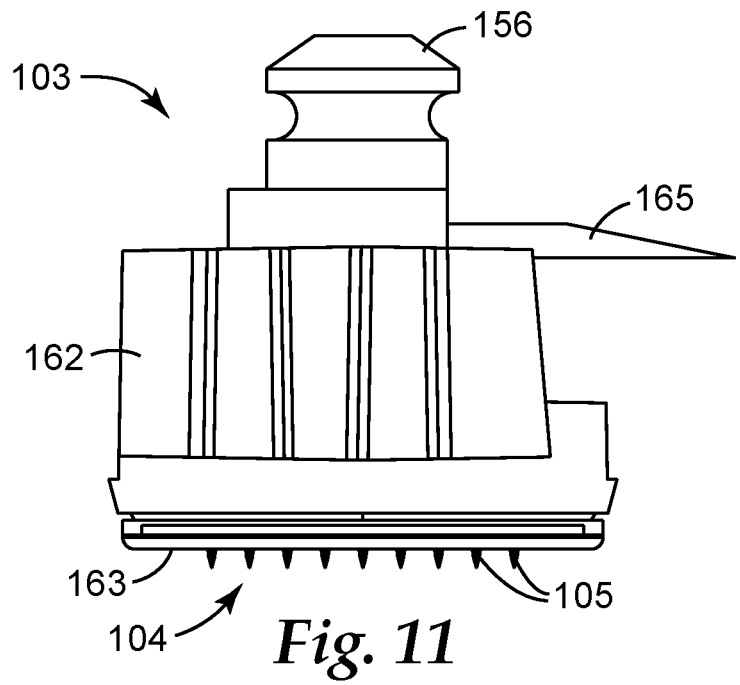
FIG. 11 is a side view of the applicator illustrated in FIG. 7.

Housing 102 also includes actuator 138 (e.g., FIGS. 1, 2 & 8). The actuator 138 has finger engageable portion 140 that is adapted to cover actuator opening 142 (e.g., FIGS. 2, 8-10) formed in upper housing portion 110. Tab portion 144 extends from finger engageable portion 140 and is hingedly connected to pivot about hinge pin 146 (e.g., FIGS. 8-10) located in upper housing portion 110. This allows actuator 138 to pivot from a position corresponding to a primed position, for example as illustrated in FIG. 9, to a position that corresponds to a position wherein hollow microneedles 105 of applicator 103 are in their penetrating position illustrated in FIG. 10.

Figure 28:
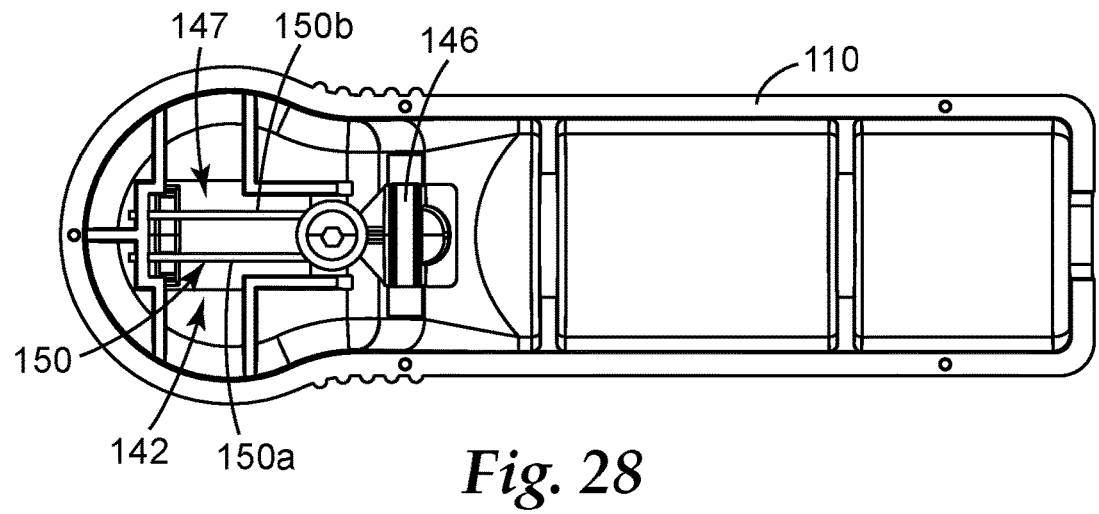
FIG. 28 is a plan view of the interior of a cover portion of the housing of the apparatus illustrated in FIG. 2.

With continued reference to FIGS. 8-10, and 28, the present description includes releasable retaining mechanism 147 for releasing first stored energy device 134 from its primed position. In the present illustrated exemplary embodiment, releasable retaining mechanism 147 may include plunger 148 depending from finger engageable portion 140. Plunger 148 is sized, shaped, and arranged to release applicator 103 when moved downwardly as by pressing down on finger engageable portion 140. During downward movement, plunger 148 engages resilient engaging device 150, such as a single piece catch spring. Resilient engaging device 150 may have a generally U-shape and may be fixed to the interior of upper housing portion 110, as by a fastener, so as to be immediately below actuator opening 142, such as illustrated in FIG. 28. Resilient engaging device 150 may include a pair of generally spaced apart and parallel resilient leg portions 150a and 150b that are adapted to be engaged and spread apart by plunger 148 when the latter is pressed downwardly therebetween. Resilient leg portions 150a and 150b are engageable with peripheral groove 151 (e.g., FIG. 9) on upper retaining member 152 of applicator 103 to form an interlocking relationship that maintains the latter in a position corresponding to a primed condition.

To release applicator 103, finger engageable portion 140 is depressed downwardly, as viewed in the drawings, such as when a user commences an infusion/injection process. As a result, plunger 148 spreads resilient leg portions 150a and 150b apart sufficiently to release them from peripheral groove 151 (e.g., FIG. 9) of upper retaining member 152. This frees first stored energy device 134 to drive or force applicator 103 downwardly, generally along vertical axis 130, so that hollow microneedles 105 can be in a released position (see, e.g., FIG. 12). The resilient leg portions 150a and 150b that are stressed when in peripheral groove 151 may return to an unstressed condition after applicator 103 has been forced by first stored energy device 134.

The present description envisions that applicator 103 may be primed before being shipped from a manufacturer or assembler of the controlled fluid release apparatus, but also allows a user to prime the apparatus in a manner to be described. When applicator 103 is to be primed, as may be described in more detail hereinafter, it will be forced (e.g., pulled or pushed) upwardly until upper retaining member 152 spreads leg portions 150a and 150b apart, whereby the latter resiliently snap into peripheral groove 151, thereby retaining applicator 103 in its primed condition. The present description envisions other kinds of releasable retaining mechanisms that may be used for releasably retaining applicator 103 in a primed condition prior to release. Such mechanisms include, but are not limited to, a wide variety of spring-biased holding members, such as latches, snap-fits, annular snap-fits, and other similar devices. It will be understood that applicator 103 need not be stored or shipped in a primed condition, but may be shipped in a non-primed condition.

Reference is now made to FIGS. 5-7, 9, 10, 12, and 13A-13C for illustrating hollow microneedles 105 of applicator 103 in a released position that may be useful, for instance, as a skin penetrating position for distributing or dispensing fluid 108 from a ready-to-use reservoir 107 to a patient. As noted, reservoir 107 may be more easily cleaned, sterilized, filled, and refilled as compared to microneedle devices having fixed or dedicated drug reservoirs integral therewith For carrying out the penetration, applicator 103 may include microneedle array 104 on the bottom or penetrating side of manifold carrier 162. In one exemplary embodiment, microneedle array 104 may be permanently attached or removably attached to applicator 103. In another exemplary embodiment, microneedle array 104 may include microneedle applicator plate 163. Formed in microneedle applicator plate 163 is an array of hollow microneedles 105 protruding therefrom.

In one exemplary embodiment, hollow microneedles 105 typically may have a length of greater than 100 µm to about 3 mm. In other embodiments, hollow microneedles 105 may have a length that ranges from about 250 µm to about 1500 mm, more typically, a length of from 500 µm to 1000 µm. In some embodiments, hollow microneedles 105 may penetrate into the skin of a patient to a depth of from about 150 µm to 1500 µm. More typically, they penetrate into the skin to a depth of from about 50 µm to 400 µm, more typically from about 100 µm to 300 µm. It will be appreciated that the depth of penetration of hollow microneedles 105 may not be the full length of the hollow microneedles themselves.

Hollow microneedles 105 may typically have a spacing of about no less than 0.7 mm on average between adjacent hollow microneedles. More typically, microneedle array 104 may have the hollow microneedles 105 spaced an average of at least 2 mm apart from each other. Hollow microneedles 105 may have an average channel bore (not shown) of 10 to 500 µm$^2$ cross-sectional area, more typically, the average channel bore may range from 80 to 300 µm$^2$. Hollow microneedles 105 may have a spacing density of 3 to 18 microneedles per cm$^2$. The bores (not shown) may allow a fluid to be dispensed at a rate of about 20 µL/min to 500 µL/min. The bore may terminate in an exit hole or port (not shown) located on a sidewall of each hollow microneedle, or a sidewall portion that is adjacent the needle tip.

The present description contemplates all forms of microneedles that can deliver fluid through them. Also, it will be understood that the foregoing values are illustrative and not necessarily limiting. It will be further understood that the present description envisions the use of other needle assemblies for injection and infusion besides hollow microneedles. As such, the needle lengths may be longer than noted above. Also, the depth of penetration of hollow microneedles 105 may vary from needle to needle. Hollow microneedles typically enable penetration into the dermis of a patient in a manner that minimizes or reduces trauma. It will be understood that a relationship of trauma and various infusion/injection parameters exist, such as is described in commonly-assigned PCT Publication No. WO2010/059605, which is incorporated by reference herein.

Reference is now made to, for example, FIGS. 12, and 13A-13C for illustrating piercing needle 165, which may comprise at least one cannula, manifold inlet tube, or other form of piercing needle. Piercing needle 165 is provided as an inlet on manifold carrier 162. Piercing needle 165 establishes a fluid path that fluidly connects fluid 108 in reservoir 107 to carrier reservoir 166 above microneedle array 104 by way of fluid pathway 168, such as illustrated. One or more piercing needles 165 are envisioned. As such, fluid 108 may be dispensed by infusion/injection into a patient's skin (signified by "S" in FIG. 12) through hollow microneedles 105. In one exemplary embodiment, piercing needle 165 may comprise lumen 170 (e.g., FIGS. 5 & 12) therethrough. Lumen 170 is connected fluidically to fluid pathway 168. Piercing needle 165 is dimensioned in length to ensure opening a sealed but openable end of reservoir 107 as will be explained below. Piercing needle 165 also has sufficient strength to accomplish this without buckling or otherwise failing. A wide variety of materials may be used for piercing needle 165. Towards this end, the materials may include, but are not limited to, metals including stainless steel, plastics, ceramics, composite materials, and combinations thereof.

Figure 12:
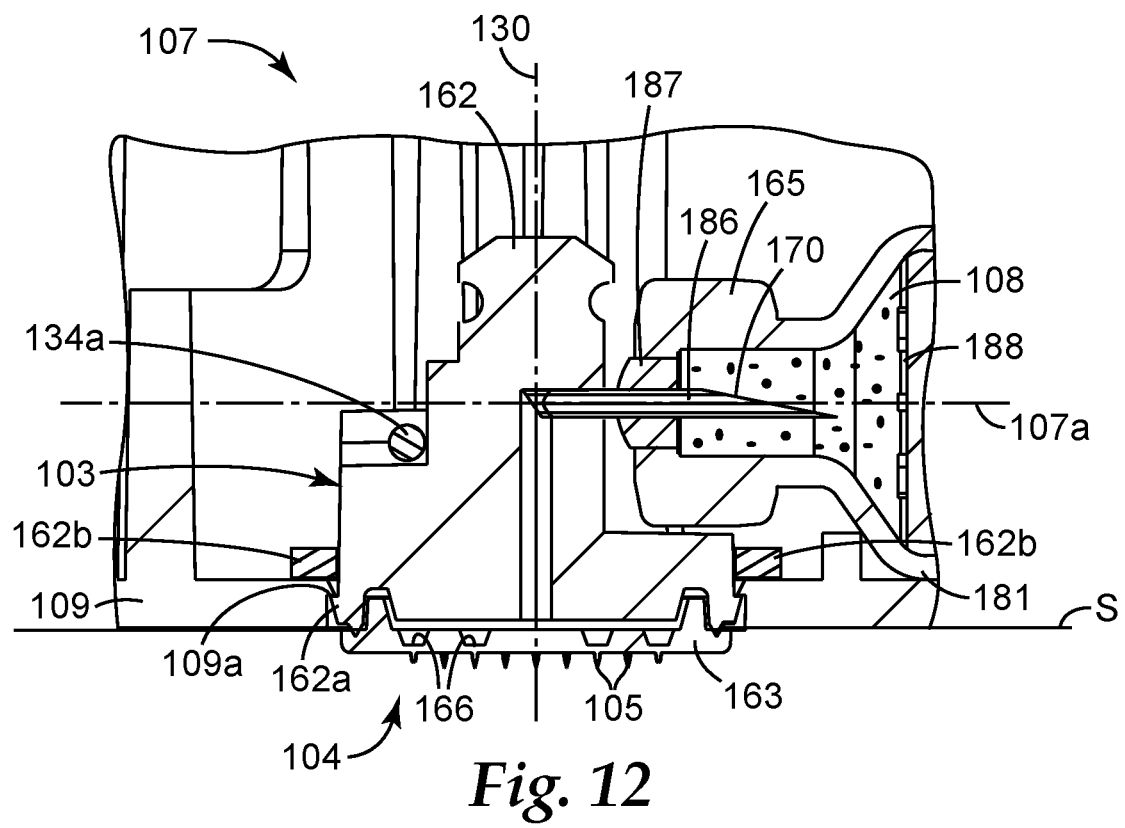
FIG. 12 is an enlarged schematic view illustrating fluid communication of a drug cartridge with an applicator.

As illustrated in FIG. 12, for example, microneedle array 104 may be fixedly connected as, for example, by ultrasonically welding it to manifold carrier 162. For example, the present description envisions holding microneedle applicator plate 163 to manifold carrier 162 by a variety of techniques including, but not limited to, snap-fits, adhesives, such as a UV curable adhesive, medical adhesives, and other similar approaches. While fixed connections are described, releasable connections may be provided, such as in situations involving reusing the controlled fluid release apparatus, whereby used microneedles may be replaced. In an illustrated embodiment, the releasable couplings include pressure-sensitive adhesives and the like.

The present description envisions positively holding manifold carrier 162 in a penetrating position for reasons that will be explained. Towards this end, manifold carrier 162 has peripheral rim portion 162a extending radially by an amount that creates a latching or interference fit, when in a released position, with corresponding retaining lower housing portions 109a (FIG. 12) of lower housing portion 109. Also, manifold carrier 162 may have annular lateral projection 162b that is adapted to engage lower housing portion 109 for even more robustly stopping microneedle carrier 162. This interference fit and/or lateral projection 162b are sufficient to stop manifold carrier 162 in a released position (useful, e.g., for penetrating a patient's skin). As such, in some embodiments, this may minimize the recoil effect of first stored energy device 134 upon release, which recoil may, if unattenuated, cause hollow microneedles 105 to dislodge from a patient's skin following impact.

Microneedle applicator plate 163 may be made from materials including polycarbonate, acrylics including polymethyl methacrylate, ABS (Acrylontitrile butadiene styrene), polypropylene, nylon, polyetheretherketone, and combinations thereof.

Figure 3:
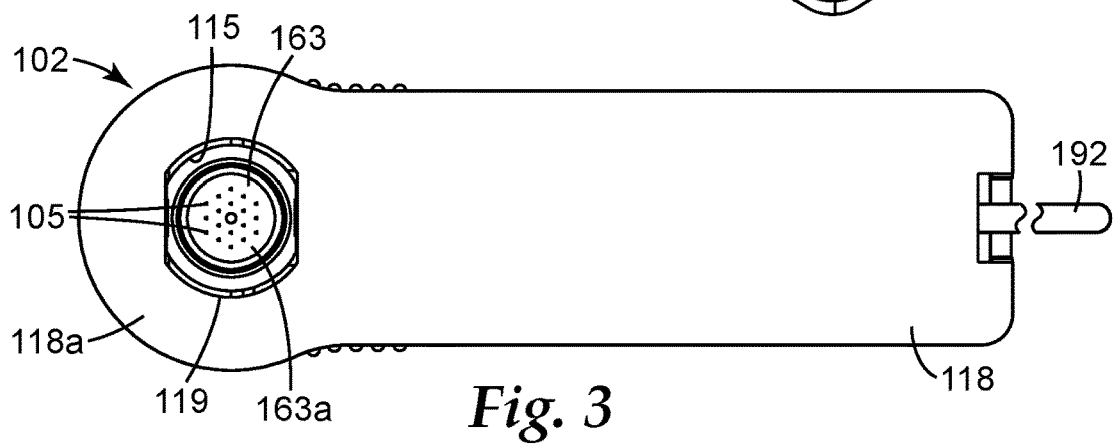
FIG. 3 is a bottom view of the apparatus in FIG. 1.
Figure 4:
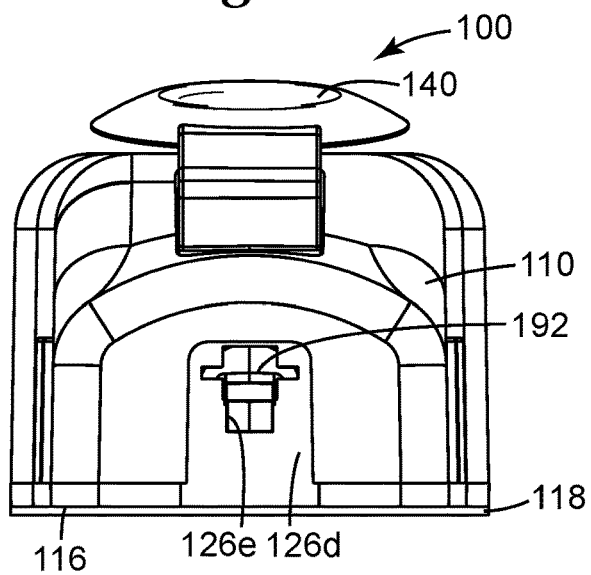
FIG. 4 is an end view of the apparatus in FIG. 1 in a primed condition.
Figure 6:
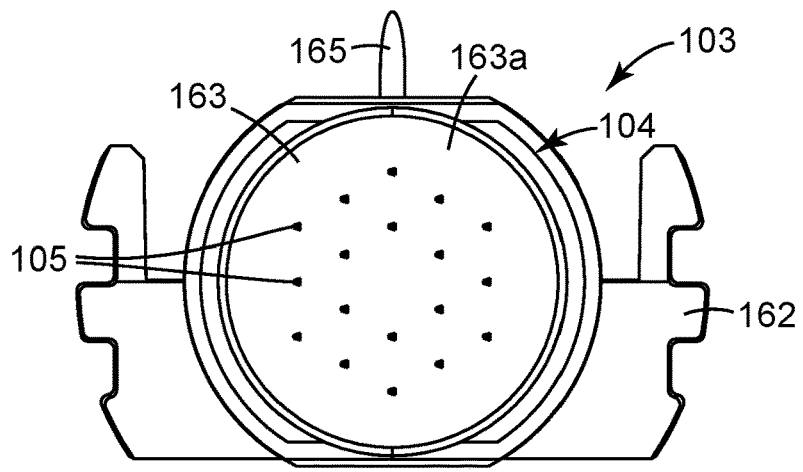
FIG. 6 is a bottom view of the applicator of FIG. 5 illustrating an array of hollow microneedles.
Figure 7:
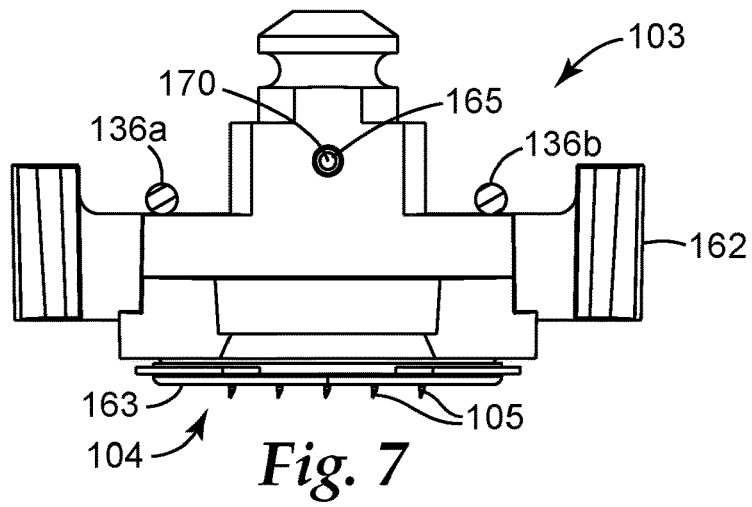
FIG. 7 is an end view of the applicator of FIG. 5 illustrating an array of hollow microneedles.

In the exemplary embodiment illustrated in FIGS. 3 and 6, microneedle applicator plate 163 has generally annular peripheral rim portion 163a free of hollow microneedles 105 and sized to enable a priming tool (FIG. 32), as will be described, to engage it, thereby enabling priming of controlled fluid release apparatus 100 as will be explained. The present illustrated exemplary embodiment illustrates peripheral rim portion 163a. It will be appreciated that other similar microneedle-free portions thereof may be provided for cooperation with a priming tool, should, for example, a pushing kind of priming tool be used. Alternatively or additionally, the present description allows for pulling of applicator 103 to its primed condition. In this regard, a tool (not shown), such as pliers or the like, may be used to pull upwardly on, for example, upper retaining member 152. Other approaches are contemplated for pushing or pulling applicator 103 for priming purposes.

Reference is now made to, for example, FIGS. 2, 9, 10, and 12. Fluid storage and delivery system 106 may include reservoir 107 that is cooperable with a second stored energy device 180. As will be described, second stored energy device 180 is operable to provide forces for opening an openable end of a reservoir to establish a fluid pathway to applicator 103 and then causing the flow of the fluid from the reservoir to the to the hollow microneedles on the microneedle applicator assembly. In this embodiment, while a single spring is illustrated, a wide variety of other approaches is contemplated as will be described.

While reservoir 107 is described in the exemplary embodiment as a drug cartridge, the present description envisions the use of a wide variety of reservoirs having a variety of sizes and constructions that function similarly. In this exemplary embodiment, reservoir 107 may include an elongated and relatively thin walled tubular glass cylinder 181. Glass cylinder 181 may be annealed, transparent, have hydrolytic resistance to the fluids being used, and be strong enough to resist cracking or otherwise bursting when pressurized in the manner as described herein. In an illustrated exemplary embodiment, glass drug cartridges typically have their lubricity enhanced, such as by using a silicone (e.g., baked and/or liquid). Other materials for the reservoir drug cartridge may include, but are not limited to, polymers of various types including a polyolefin to avoid reaction to contained fluids. Polymers normally possess friction coefficients that permit piston travel.

Glass cylinder 181 has end 182 that is openable and plunger end 184. Openable end 182 is typically closed and sealed by end cap 185. End cap 185 may be secured to a neck portion of glass cylinder 181 at end 182. End cap 185 may include metallic cap 186, such as an aluminum cap, that is crimped to end 182 in a known manner. End cap 185 may hold septum 187 (e.g., FIG. 12) that sealingly closes an otherwise open end 182.

Septum 187 may be made of many different materials including those typically used with reservoirs (e.g., drug cartridges). Septum 187 may be made of a pierceable and resealable elastomeric seal or septum that is securely mounted, with or without being crimped, across end 182. Typically, elastomers may be crimped onto an end of a glass cylinder, with material, such as aluminum. Other similar septum materials and modes of securing it to the end of the glass cylinder 181 may be used. For example, a molded-in septum of a material may be used, such as West Pharmaceutical Services, Inc, so-called CZ series, a cap, such as a standard syringe luer cap, or a molded end thin enough to be pierced. A variety of materials may be used that are subject to piercing with sufficient piercing force and which may maintain a seal once pierced. As noted, septum 187 is pierced during use and seals the piercing needle with enough force to prevent leakage during transfer of fluid from reservoir 107. Some known septum materials are contemplated that allow the septum to reseal following withdrawal of a needle after use. The present description envisions unsealing or opening the otherwise closed septum 187 by a variety of approaches.

Reservoir 107 includes piston 188 that is in sliding and sealing relationship with respect to interior walls of glass cylinder 181. This provides adequate sealing for a fluid storable in an interior variable volume chamber formed between piston 188 and end 182. The chamber may be sized to have a volume of fluid to accommodate an intended dosage(s). Such a reservoir 107 (e.g., a drug cartridge) may be of the type wherein pre-filled drugs are ready-to-be used, such as the fluids noted above. Glass cylinder 181 may be of the kind that satisfies standards, including international standards, such as the International Organization for Standards (ISO). In addition, glass cylinder 181 is relatively easily cleanable and sterilizable which are highly advantageous features should it be desirable to reuse. Other components of reservoir 107 may also be made to satisfy standards, such as ISO standards.

Drug cartridges of the kind noted offer advantages in that they are ready-to-use, versatile from the standpoint that the medical community tends to use them relatively easily and economically in supplying fluids and dosages that are customizable to individual patients. Also, such drug cartridges may be reusable following cleaning and sterilization by techniques known in the industry. This kind of drug cartridge may be easily refilled by known approaches utilized in the field. As such, its use in the controlled fluid release apparatus of the present description provides several significant advantages.

While not shown, the present description also envisions the use of valve mechanisms for opening an openable end of a drug cartridge or reservoir for allowing transferring of a fluid to the hollow microneedles. For example, a valve member retained in a reservoir similar to the drug cartridge may be opened from a fluid blocking or closed condition by having it cooperate with structure (not shown), for example a cannula, on the microneedle applicator assembly, as the two are brought into operative engagement. However, piercing a sealing septum, as noted above, is a simplified and cost effective approach for establishing fluid communication.

Referring back to piston 188, it is adapted to travel along a length of reservoir 107 until fluid 108 is completely (or nearly completely) forced or expressed therefrom. Typically, piston 188 may be made of materials that seal against the body of reservoir 107, but are also inert with respect to the fluid. For example, purified cyclo-butyl materials may be typically used for such pistons, but silicones are also contemplated. Other similar materials include, but are not limited to, polypropylene, methlypentene, cyclic olefin polymers, and cyclic olefin copolymers. In addition, piston 188 may be made of diverse materials including laminated constructions. While the illustrated embodiment uses one kind of piston, others may be utilized.

Figure 26:
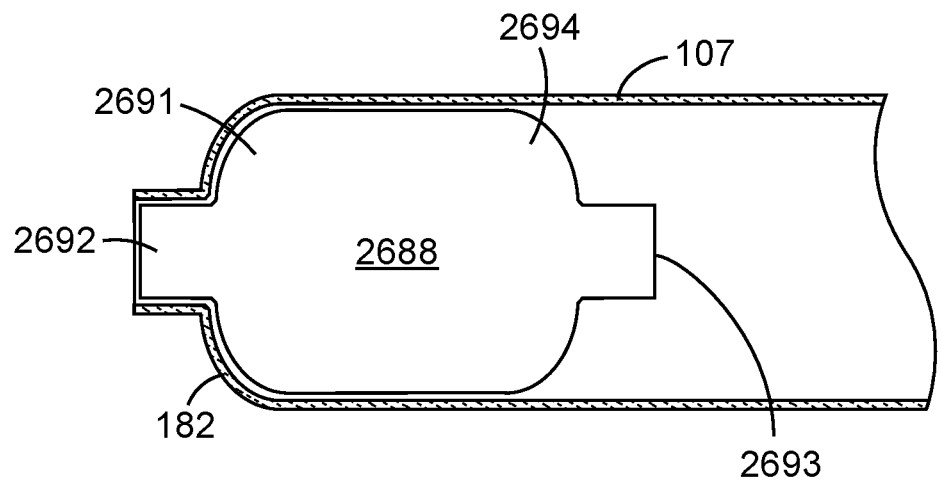
FIG. 26 is a schematic view of a contoured piston.

For example, reference is now made to FIG. 26 for illustrating an alternative piston 2688 that may be used. Piston 2688 may have forward end 2691 with nose portion 2692 contoured to substantially match the interior shape of necked end portion 182 of reservoir 107. This facilitates substantially complete emptying of the fluid from reservoir 107. As such, issues concerning excess fluid remaining in reservoir 107 are reduced. Piston 2688 may also have second nose portion 2693 at an opposing longitudinal end portion 2694 thereof. This may enhance versatility of piston 2688. Piston 2688 may be made of a variety of materials including, but not limited to, plastic resins, such as polypropylene, methylpentene, cyclic olefin copolymers that are relatively easily molded. Other similar materials may be used.

Reference is made back to FIGS. 8-10, 12, and 13A-13C. Reservoir 107 has longitudinal axis 107*a* that is, in one exemplary embodiment, adapted to be generally parallel to a patient's skin S as well as housing 102. Of course, reservoir 107 may be disposed at other angles relative to the skin and the housing assembly. Such angling may allow, for instance, for allowing gravity to assist in the evacuation of reservoir 107. For further keeping a low profile of controlled fluid release apparatus 100, longitudinal axis 107*a* is generally normal to vertical axis 130. In some respects, this compact geometric arrangement is advantageous. Reservoir 107 is a transparent glass drug cartridge, in one exemplary embodiment, for enabling visual observations relating to the progress of fluid dispensing. This is advantageous particularly in infusion situations that may take relatively long periods. Such a glass drug cartridge may be of a commercially available type, such as from Schott North America, Elmsford, N.J., USA, and West Pharmaceutical Services, Inc. of Lionsville, Pa., USA. Other kinds of reservoirs having similar properties are envisioned.

Reservoir 107, when made of glass, may also be advantageous in regard to enhancing the versatility of the controlled fluid release apparatus 100. An advantage offered by the present description is that reservoirs 107 have sizes and shapes many pharmacists in the field are typically familiar with in regard to filling them. Also, because reservoir 107 may be separate from controlled fluid release apparatus 100, users may be able to use reservoirs particularly formulated for themselves and then easily install them in the controlled fluid release apparatus. Moreover, by being able to use known drug cartridges, patients are able to use a wide variety of drugs and dosages dispensed in a manner particularly tailored to them and not be dependent on a manufacturer of the dispensers having fixed reservoirs. The present description is in sharp contrast to known microneedle apparatus and systems that have dedicated or fixed fluid reservoirs of preselected sizes. Further, the latter category may additionally require special efforts to fill, as well as sterilize and refill.

A glass drug cartridge reservoir 107 may have dimensions that range from about 2 cm to about 7 cm in terms of their lengths, and may have inner diameters that range from about 4 mm to about 12 mm. More typically, the lengths may range from 4 cm to 6 cm, and the inner diameters from about 6 mm to about 10 mm. The present description contemplates other dimensions depending on, for example, the size of the drug dispensing cartridges. While a transparent glass drug cartridge reservoir 107 may be utilized, other materials may also be used. These materials and construction should be compatible to the fluids contained, and be able to withstand the pressures generated during use.

Also, while drug cartridges may be transparent, they need not be, but could instead be provided with a window(s) for allowing observations of the piston forcing the fluid during the dispensing process. Also, the present description envisions that other kinds of generally tubular containers may be used as well that are consistent with the present description. This is significant in terms of overall versatility in treating patients.

The present description envisions a controlled fluid release apparatus 100 that contemplates single-use for such drug cartridges, but also replacing them, much like cassettes. By separating the drug cartridge from the other portions of the controlled fluid release apparatus, the two can be made independently and are more easily customized to accommodate a variety of factors including, but not limited to, a variety of drugs, patients, as well as infusion times.

In the illustrated embodiment, spring release 190 (e.g., FIG. 29) is operated to release second stored energy device 180. As will be explained, the stored fluid in reservoir 107 will be released following establishment of a fluid passage by the cooperation of piercing needle 165 with septum 187. In one exemplary embodiment, second stored energy device 180 may include an elongated coil spring. Second stored energy device 180 may be released by spring release 190. Spring release 190 may include latch 192 that is attached at one end to plunger 194 abutting piston 188. Second stored energy device 180 is interposed between plunger 194 and rear wall portion 126*d* to be loaded in a manner that provides sufficient operating forces for displacing reservoir 107 when second stored energy device 180 is released by spring release 190.

Latch 192 and plunger 194 may be separate from each other but may be coupled. They may be made of similar or dissimilar materials, such as suitable plastics and metal. Latch 192 may be elongated as illustrated or may have a shorter length. A longer length facilitates removal of second stored energy device 180 from reservoir 107 as will be described. Projection 196 of latch 194 is coupled to rear wall portion 126*d* (FIG. 9), thereby retaining second stored energy device 180 in a latched and loaded condition. While projection 196 on latch 192 is illustrated for cooperating with the retaining wall, the present description envisions other spring release mechanisms, similar to the kinds defined above.

To release second stored energy device 180, a user merely lifts latch 192 from engagement with the rear wall portion 126*d*. Second stored energy device 180 then displaces reservoir 107 axially until it reaches stop 126*f* (FIG. 13A-13C) on lower housing portion 109.

Figure 13A:
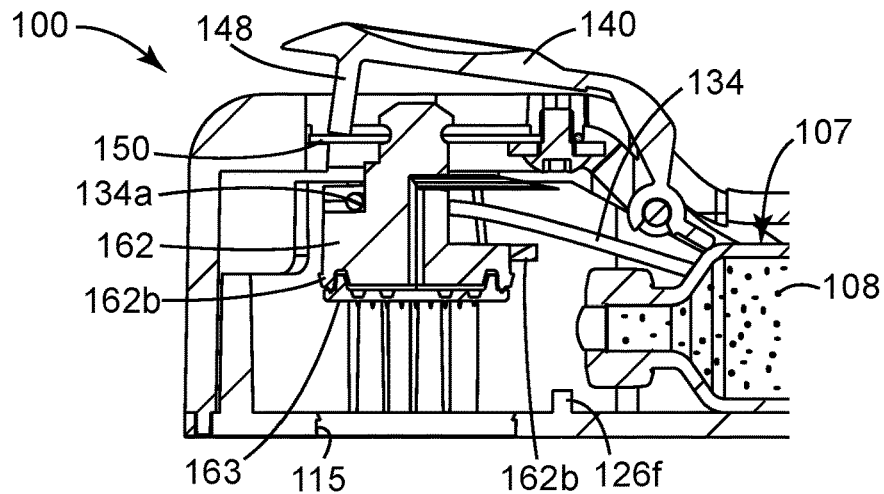
FIG. 13A is a fragmented view in cross-section of an apparatus in a primed condition.
Figure 13B:
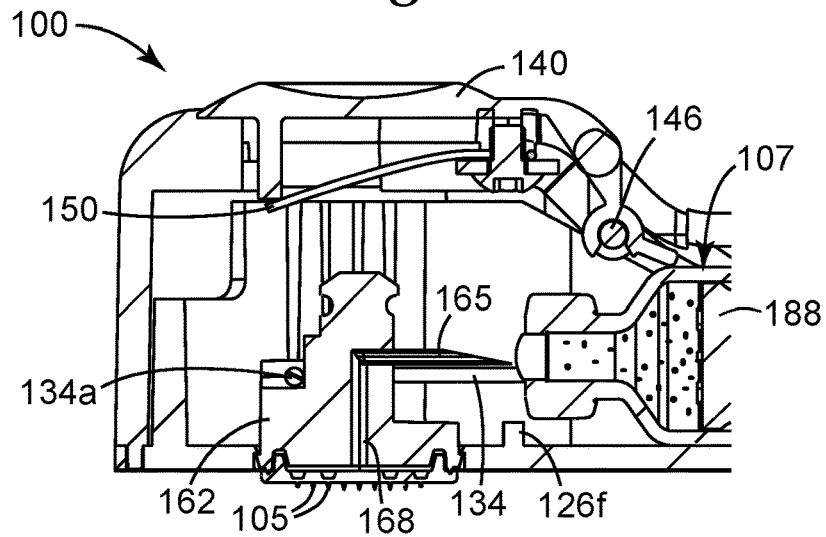
FIG. 13B is a fragmented view in cross-section of an apparatus illustrating hollow microneedles penetrating.
Figure 13C:
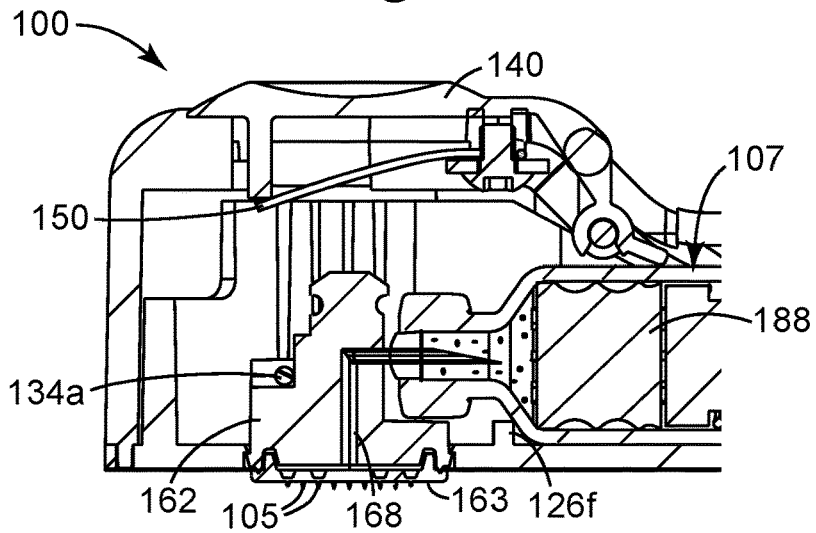
FIG. 13C is a fragmented view in cross-section of the apparatus showing transfer of the fluid from a drug cartridge to the applicator.
Figure 14:
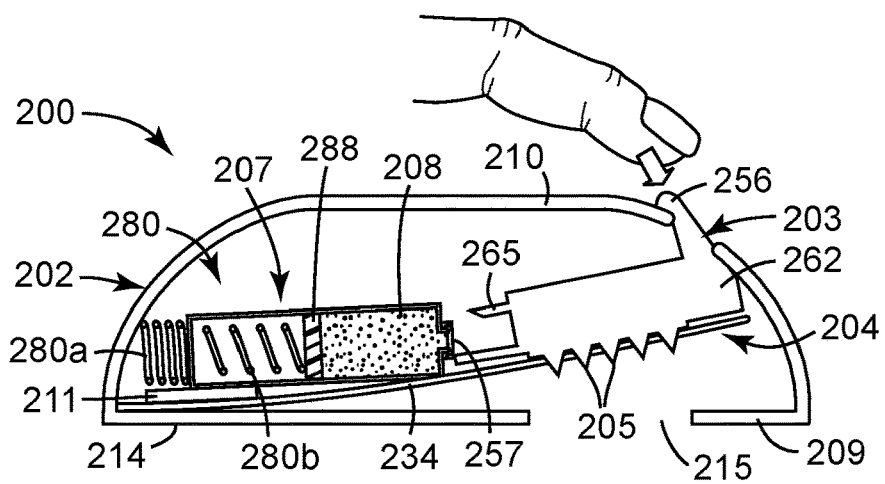
FIG. 14 is a schematic view of an exemplary embodiment of an apparatus according to the present description in a primed condition.
Figure 15:
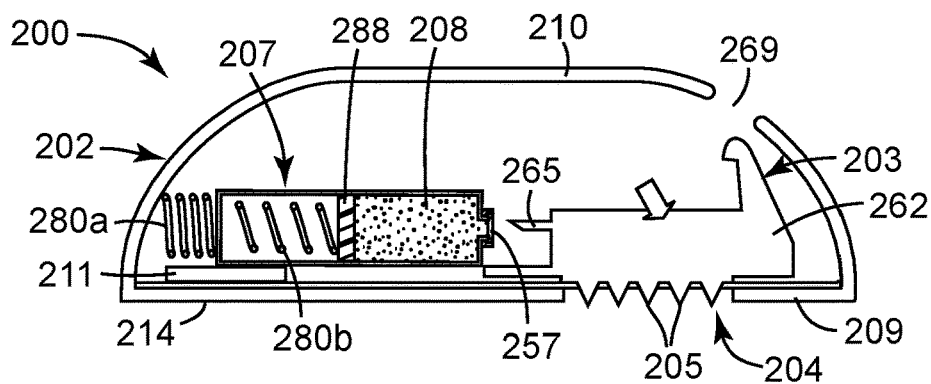
FIG. 15 is a schematic view of an exemplary embodiment of an apparatus according to the present description where the first stored energy device is actuated.
Figure 16:
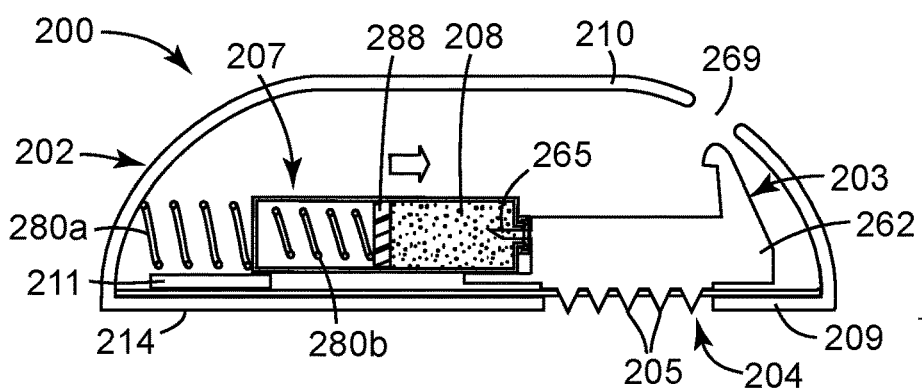
FIG. 16 is a schematic view, similar to FIG. 15 but illustrating actuation of the second stored energy device.
Figure 17:
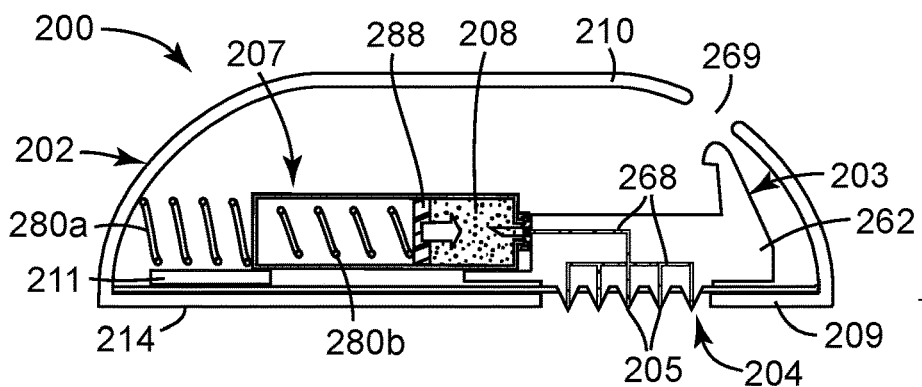
FIG. 17 is a schematic view similar to FIG. 16 but illustrating displacement of a piston.

Piercing needle 165 pierces septum 187 after applicator 103 has reached its penetrating position (see FIGS. 10, 13B, 13C). A fluid passage is established between the reservoir and the microneedle applicator for communicating fluid therebetween. As a result, the fluid is forced through the now opened septum 187 under the influence of second stored energy device 180 pushing piston 188. The fluid may enter piercing needle 165 and second stored energy device 180 is allowed to force piston 188 forwardly to compress the chamber and force fluid therefrom into applicator 103. From piercing needle 165, the fluid flows into fluid pathway 168 and carrier reservoir 166 into hollow microneedles 105. Because of the automatic operation provided by second stored energy device 180 on reservoir 107, the forces acting on the system can be controlled generally regardless of user-applied forces. This is advantageous over other systems that require manual pushing and/or sliding of a member in order to affect a release and dispensing of fluids. As noted, manual pushing or pulling forces may inadvertently cause issues. As such, this may cause the hollow microneedles to dislodge, thereby defeating the intended results of the apparatus.

To replace used drug cartridges, a user may pull on latch 192 with a suitable hand tool (not shown) to recompress second stored energy device 180. As such, a user can separate the piercing needle and the septum. Consequently, reservoir 107 and latch 192 may be removed. It will be understood that a new drug cartridge may be replaced in the controlled fluid release apparatus 100 for the one removed. Thus, a user need only replace a cartridge instead of ordering a new device. In regard to adding a new drug cartridge, second stored energy device 180 may be reused as well as the latch 192 and plunger 194. Also, microneedle array 104 should be replaced as well.

Consequently, the manufacturer or even the user may easily install a ready-to-use reservoir 107. This may be accomplished by inserting a drug cartridge and then inserting a second stored energy device in their illustrated positions. By allowing reservoir 107 and second stored energy device 180 to be installed separately, shelf life is enhanced since there is not a requirement for the coil spring to be constantly loaded against the drug cartridge for long periods.

The first and second stored energy devices of the present description may be comprised of at least one stored energy device from a group consisting of: spring devices, gaseous propellants, chemicals, electrical devices, and combinations thereof.

Figure 22:
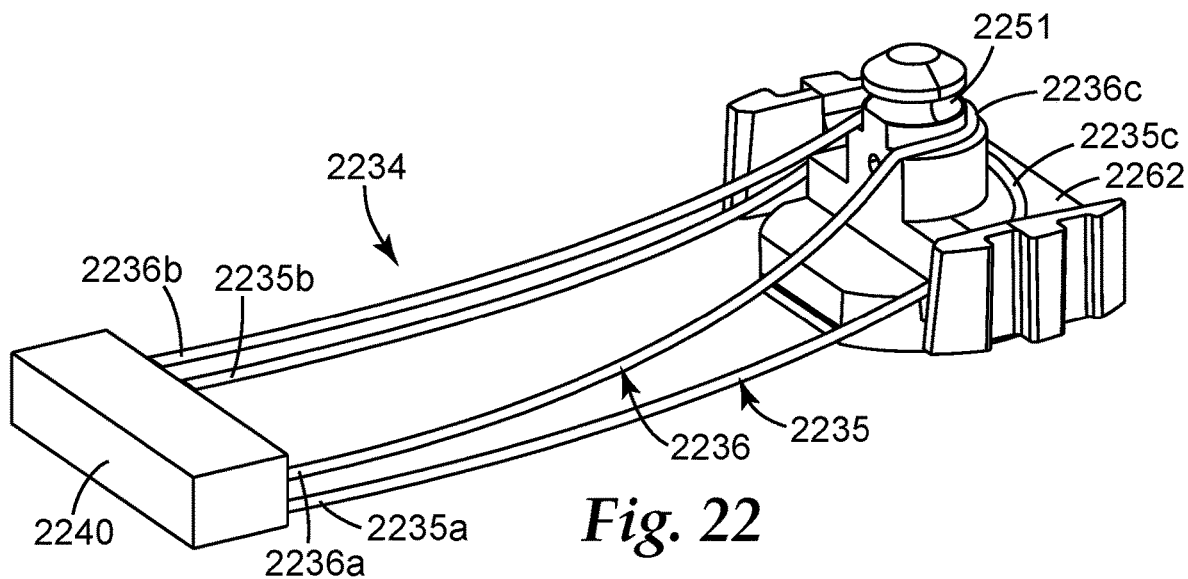
FIG. 22 is an enlarged view of yet another exemplary embodiment of a spring device of the present description.
Figure 23:
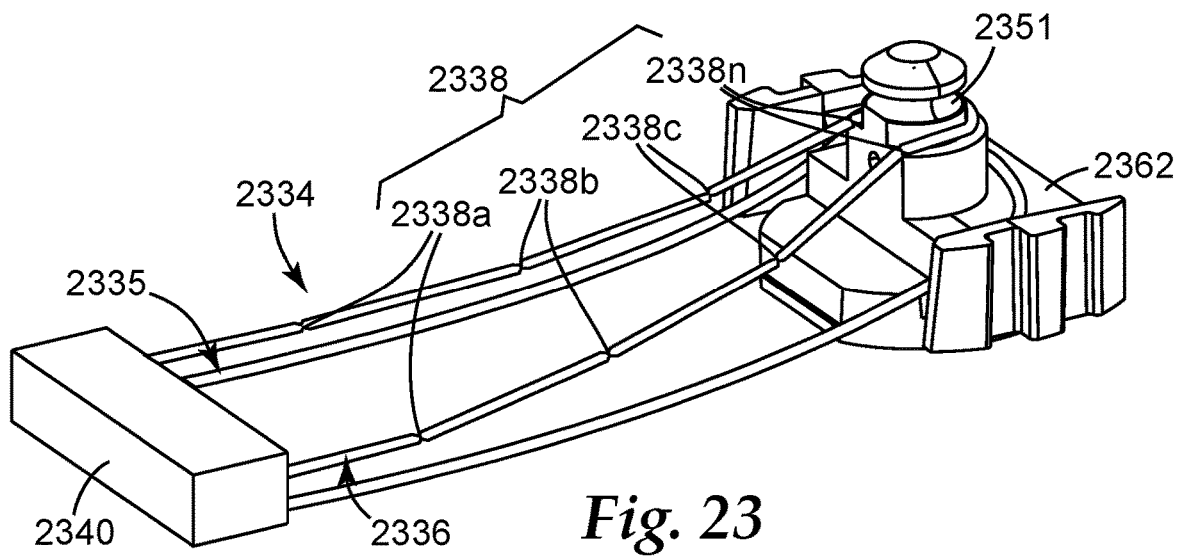
FIG. 23 is an enlarged view of yet another exemplary embodiment of a spring device of the present description.

Reference is now made to FIGS. 22 and 23 for illustrating alternative exemplary embodiments of a first stored energy device 2234 and 2334, respectively. Stored energy device 2234 may be arranged to provide a parallelogram assembly configuration that includes two generally similar leaf-like springs 2235 and 2236. Leaf-like spring 2235 has proximal ends of generally parallel leg portions 2235a and 2235b attached to mounting block 2240 on the lower housing portion, while bight portion 2235c rests on manifold carrier member 2262. Leaf-like spring 2236 has proximal ends of leg portions 2236a and 2236b attached to mounting block 2240 while bight portion 2236c rests on manifold carrier 2262 below groove 2251. This parallelogram configuration provides sufficient forces to drive the hollow microneedles on a manifold carrier into a released position (e.g., for penetration of the skin). The parallelogram configuration tends to simplify construction inasmuch as it does not allow any appreciable lateral shifting during operation thereof, thereby obviating need for having manifold carrier 2262 cooperate and be guided by a housing assembly. As such, stored energy device 2234 allows manifold carrier 2262 to be used without guiding provided by channels formed on the housing assembly (not shown).

FIG. 23 is another exemplary embodiment of stored energy device 2334 and is similar to FIG. 22. Similar reference numerals will be used for similar parts, except that the prefix "22" will be replaced with the prefix "23". Stored energy device 2334 is a parallelogram relationship including leaf-like springs 2335 and 2336. One difference between this embodiment and the previous one is that leaf-like spring 2336 may be molded to have one or more living hinges 2338a, 2338b, 2338c, through 2338n (collectively, 2338) thereon. Living hinges 2338 act to move manifold carrier 2362 in a predetermined way each time along the axis. It will be appreciated that other parallelogram constructions may be provided as well as other arrangements of spring devices, which enable controlled movement of manifold carrier 2362 without need for guidance, by a housing or the like.

Reference is now made to FIGS. 14-17 for illustrating another exemplary embodiment of controlled fluid release apparatus 200 of the present description. This embodiment differs from the preceding one in several respects including being able to affect dual automatic operation in response to a user merely activating a single actuation device.

Similar reference numerals will be used for similar parts, except that the prefix "2" will replace the prefix "1". In this exemplary embodiment, provision is made for controlled fluid release apparatus 200 to comprise housing 202, applicator 203 connected to microneedle array 204 carrying one or more hollow microneedles 205, and reservoir 207. Included is first stored energy device 234 for forcing hollow microneedles 205 of applicator 203 into a patient's skin, and second stored energy device 280 that is comprised of a pair of spring devices 280a and 280b. First spring device 280a may be a coil spring suitably interposed between housing 202 and reservoir 207 to force the latter, as will be explained, to pierce a septum for establishing fluid communication with microneedle array 204. Second spring device 280b may be another coil spring for forcing piston 288 within reservoir 207 that forces piston 288 to expel or force fluid 208 into microneedle applicator 203.

Housing 202 includes lower housing portion 209 and upper housing portion 210 that may be matable to form a self-contained, microneedle controlled fluid release apparatus 200 such as illustrated. As will be evident, single actuation enables dual automatic operation of the components to deliver the fluid into a patient's skin.

In one embodiment, lower housing portion 209 may be planar and have opening 215 for allowing penetration of microneedles. Base 214 may completely cover the open end of upper housing portion 210. A pair of generally parallel and spaced apart leaf-like springs may form first stored energy device 234 (only one of which is shown) may be directly coupled at their proximal ends to base 214 for carrying applicator 203 as illustrated.

Applicator 203 is suitably mounted on distal ends of first stored energy device 234, whereby hollow microneedles 205 may pass therebetween. Applicator 203 may include a lightweight hollow or solid plastic manifold carrier 262 having piercing needle 265 that is to penetrate septum 287 of reservoir 207. In this embodiment, manifold carrier 262 may include fluid pathway 268, such as illustrated, that lead to hollow microneedles 205. The bottom leaf-like springs in the illustrated first stored energy device 234 possess spring-like characteristics similar to the leaf springs of the earlier embodiment. Applicator 203 may also include upstanding latch 256 protruding from a top portion thereof. Latch 256 is adapted to extend through opening 269 in upper housing portion 210 and engage a projection (not shown) on upper housing portion 210 to maintain a latched condition. In the latching process, the leaf-like springs of first stored energy device 234 flex as latch 256 is latched to a top portion of upper housing portion 210 (see FIG. 14). This latching position corresponds to a primed and loaded condition for the controlled fluid release apparatus 200.

Reservoir 207 may be mounted so as to have its longitudinal axis generally parallel to a patient's skin surface. Housing 202 may also have an adhesive layer (not shown). Reservoir 207 is mounted on support 211 of upper housing portion 210 to have limited sliding movement relative thereto. Applicator 203 has stop 257, which engages a forward portion of reservoir 207 to prevent forward movement of the latter when engaged therewith. When latch 256 is released, applicator 203 may move automatically into a skin penetrating position (FIGS. 15-17) under the influence of the leaf-like springs of first stored energy device 234. This frees stop 257 from its blocking arrangement with reservoir 207. As such, reservoir 207 is driven by first coil spring 280a so that piercing needle 265 can penetrate septum 287, thereby allowing fluid 208 to flow therefrom. Second coil spring 280b in response to this piercing, forces piston 288 to expel fluid 208 into the applicator 203. In this embodiment of reservoir 207, both ends of a glass cylinder may have their ends closed, wherein one of the closed ends may be adequate for storing second coil spring 280b.

Figure 18:
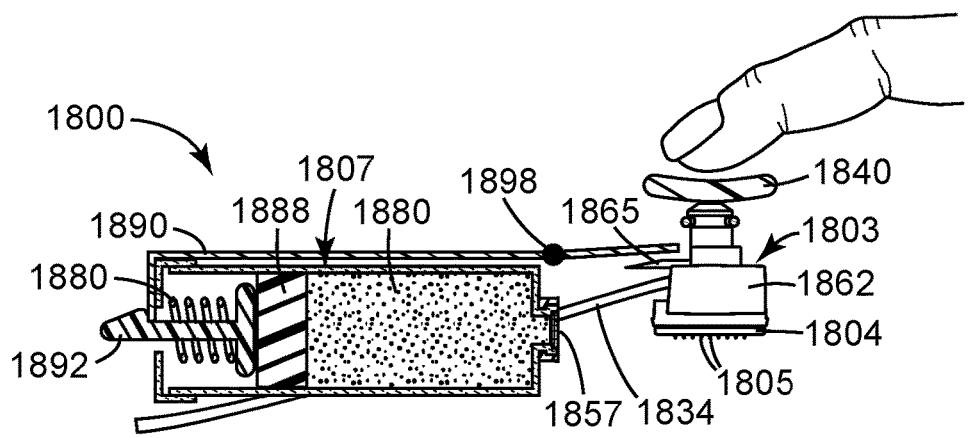
FIG. 18 is a schematic view of another exemplary embodiment of an apparatus according to the present description.
Figure 19:
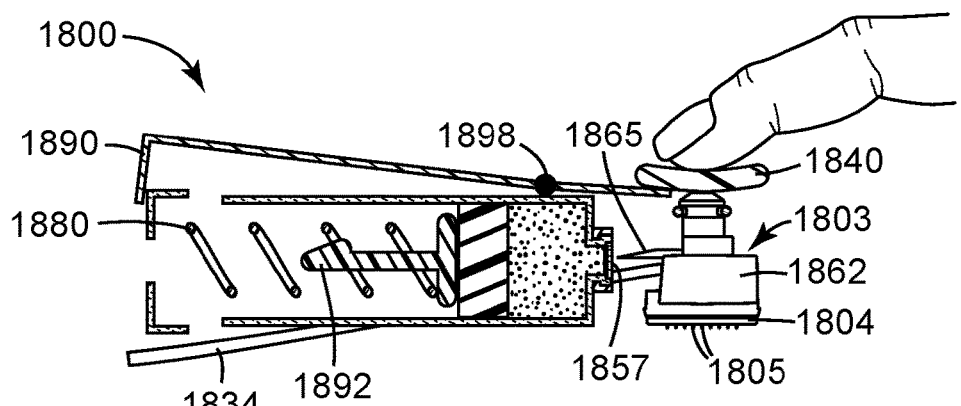
FIG. 19 is a schematic view of an actuated apparatus.

Reference is made to FIGS. 18 and 19 for illustrating another exemplary embodiment of a schematic representation of controlled fluid release apparatus 1800. Similar reference numerals will be used for similar parts, except that the prefix "18" will replace the prefix "1". This exemplary embodiment allows a single actuation of a single actuator to be responsible for commencing dual automatic operation of the microneedle penetration as well as the release and dispensing of the fluid from reservoir 1807. Restraining lever 1890 has one end releasably cooperating with a projection on latch 1892 and another end engageable by single actuator 1840. By manually pressing on single actuator 1840, a restraining spring is overcome and first stored energy device 1834 is then free to force manifold carrier 1862 into engagement with the skin.

Further downward displacement of actuator 1840 pivots restraining lever 1890 at pivot 1898, which in turn removes restraining lever 1890 from interfering with latch 1892. It will be appreciated that other mechanisms may be used to release the second stored energy device in response to depressing single actuator 1840 besides restraining lever 1890. Consequently, second stored energy device 1880, such as a coil spring, is released to displace reservoir 1807 whereby piercing needle 1865 penetrates septum 1887. As a result, second stored energy device 1880 forces piston 1888 to expel fluid 1808 from reservoir 1807 into applicator 1803.

Figure 20:
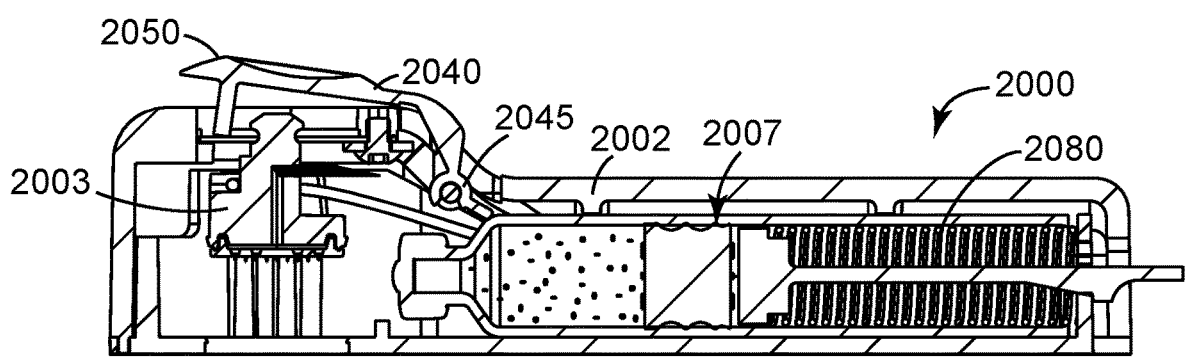
FIG. 20 is an elevation view in cross-section of another exemplary embodiment of an apparatus of the present description having portions removed for clarity.
Figure 21:
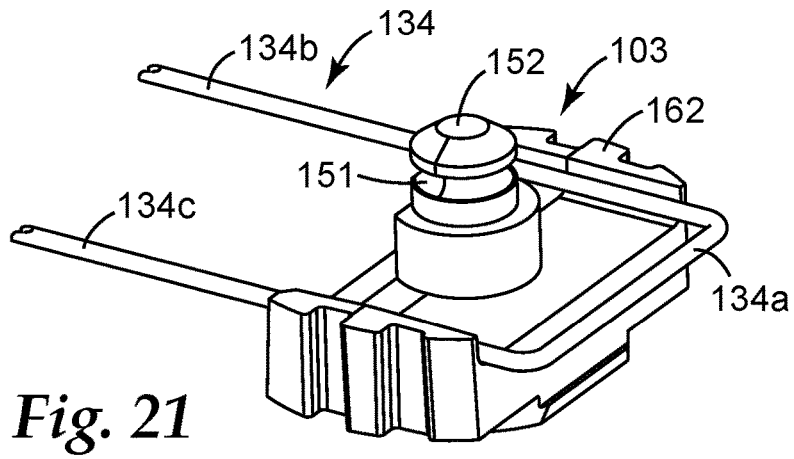
FIG. 21 is an enlarged view of a U-shaped, leaf-like spring device of the present description.

Reference is made to FIG. 20 for schematically illustrating yet another exemplary embodiment of controlled fluid release apparatus 2000 of the present description. Similar reference numerals will be used for similar parts, except that the prefix "20" will replace the prefix "1". This embodiment is similar to the last insofar as a user merely has to activate single actuator 2040 for initiating the dual automatic operations noted previously. In this exemplary embodiment, provision is made for housing 2002, applicator 2003, reservoir 2007, fluid 2008, first stored energy device 2034, and second stored energy device 2080. One difference between this embodiment and that shown in FIG. 2 is that latch 2092 no longer functions to latch reservoir 2007 in a stationary position. Instead, finger engageable portion 2040 is provided with restraining finger 2045 that engages a forward end portion of reservoir 2007 to maintain the latter at rest when applicator 2003 is in the primed condition. When a user depresses finger engageable member 2040, catch spring 2050 is released which allows the leaf-like spring of first stored energy device 2034 to force applicator 2003 from a primed position to a position where the hollow microneedles 2005 may penetrate a patient's skin. Sequentially or substantially simultaneously, restraining finger 2045 is pivoted upwardly away from engagement with reservoir 2007. This allows the second coil spring of second stored energy device 2080 to displace reservoir 2007 as in the previous embodiment of FIGS. 1-13C to commence the fluid releasing and dispensing operations from the drug cartridge as described above. It will be understood that the present description envisions a wide variety of approaches to release the first and second stored energy devices in response to a single actuation so that they can initiate their noted automatic operations in a controlled manner.

Figure 27:
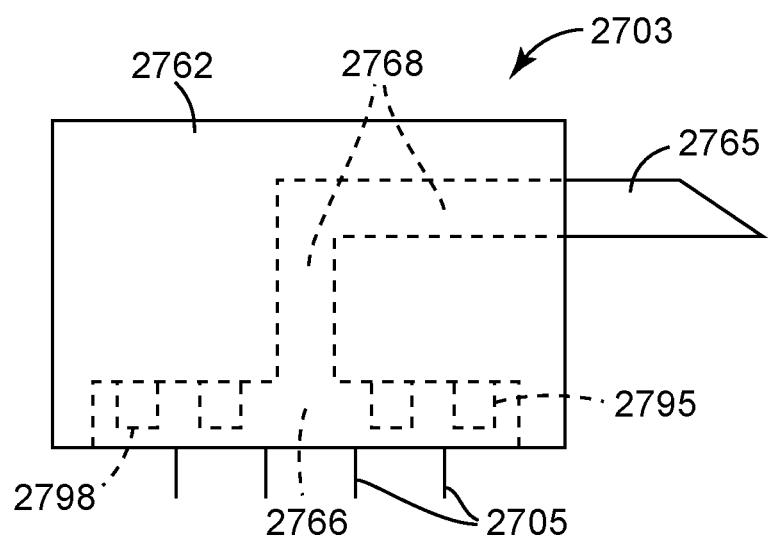
FIG. 27 is a schematic view of projections in the applicator for reducing any excess fluid remaining therein.

An alternative approach is illustrated in FIG. 27 that schematically illustrates another exemplary embodiment of manifold carrier 2762 that is similar to manifold carrier 162. This embodiment is for reducing excess fluid remaining in the drug cartridge and fluid passages of applicator 2703.

As noted earlier, minimizing excess fluid remaining in the drug cartridge and fluid passages of the microneedle applicator assembly is useful in reducing costs associated with dispensing drugs. Essentially, manifold carrier 2762 may include piercing needle 2765 in fluid communication with fluid pathway 2768 to carrier reservoir 2766. One or more of projections 2795 integrally formed on manifold carrier 2762 in carrier reservoir 2766 minimizes the space of the latter. Projections 2795 are constructed to allow fluid flow, but minimize trapping of any fluid therebetween. In this regard, projections 2795 are appropriately sized, shaped, and spaced relative to each other to ensure passage of the fluid to provide the infusion, yet avoid trapping of pockets of fluid including air. As such, a likelihood of so-called excess fluid remaining in a reservoir (e.g., a drug cartridge) and fluid pathways is minimized. This may be significant as, for example, when the fluid is insulin.

Further, projections 2795 may, in some embodiments, minimize the likelihood of introducing air through hollow microneedles 2705 and negatively affecting infusion of the fluid. Also, the present description envisions constructing manifold carrier 2762 so as to minimize excess fluid remaining in the reservoir and fluid pathways of manifold carrier 2762 by placing a septum of reservoir 107 less than about 10 mm from manifold carrier 2762. Also, manifold carrier 2762 eliminates tubing. This is another approach for minimizing excess fluid.

Reference is made to FIGS. 25A, 25B, 30, and 31 for illustrating different kinds of stored energy device arrangements for the second stored energy assembly or device.

Instead of the pair of springs illustrated in FIGS. 14-18, the present description also envisions using the pair of first and second spring devices illustrated in FIGS. 25A, 25B for effecting the piercing action and the fluid infusion. For example in FIG. 25A, a piercing spring 2500 is provided for driving a drug cartridge (not shown) and this may be spiral spring 2500. The infusion spring 2502 for forcing a piston may be a coil spring 2502. In FIG. 25B, the piercing spring 2600 may be a Belleville spring 2600 and the infusion spring 2602 may be a coil spring 2602. The foregoing arrangements may achieve the piercing and infusion in a reliable and compact manner.

Figure 30:
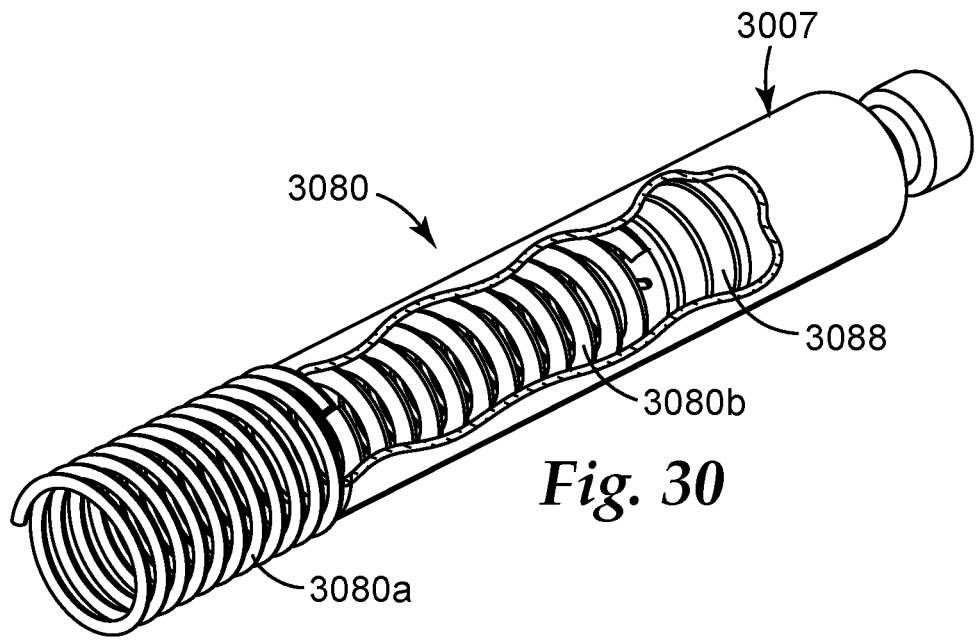
FIG. 30 is a view illustrating an exemplary embodiment of a pair of spring devices as a second storage energy device.

FIG. 30 illustrates another pair of first and second spring devices that act as second stored energy device 3080. Second stored energy device 3080 may be formed as a single member having first and second spring portions 3080a, 3080b, each having a different diameter and strength than the other for effecting the piercing and the infusion or fluid delivery. For example, first spring portion 3080a may act as the piercing portion that cooperates with one end portion of reservoir 3007, to drive the latter, whereby its septum (not shown) will be penetrated by a piercing needle (not shown). Second spring portion 3080b that contacts piston 3088 serves to act as the infusion spring for forcing the fluid from reservoir 3007 once a piercing needle and septum establish a fluid pathway as noted above.

Figure 31:
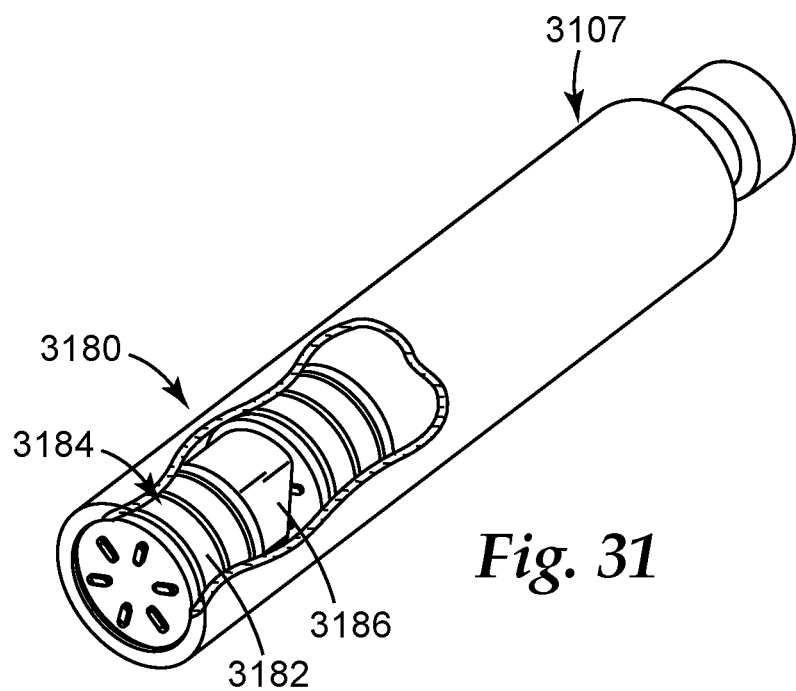
FIG. 31 is a view illustrating a gaseous propellant as a second storage energy device.

FIG. 31 illustrates an embodiment wherein a piercing spring and infusion spring for acting on reservoir 107 have not been depicted. This embodiment differs from the above in that gaseous propellant mechanism 3180 serves as both the piercing spring and the infusion spring. Gaseous propellant mechanism as second stored energy device 3180 includes stopper 3182 that is disposed to remain stationary at the end of reservoir 3107. The gaseous propellant mechanism of second stored energy device 3180 includes gas container 3184 that will emit the gaseous contents in response to being activated. Activation of the gaseous propellant mechanism of second stored energy device 3180 may be by any known approach in response to actuation by a spring like device (not shown). Once activated the gaseous contents, such as DuPont Dymel 236fa will be released from gaseous bag 3186 and generate sufficient forces to effect displacement of the drug cartridge and the piston thereof.

The gaseous propellant mechanism of second stored energy device 3180 may be a known kind.

Figure 32:
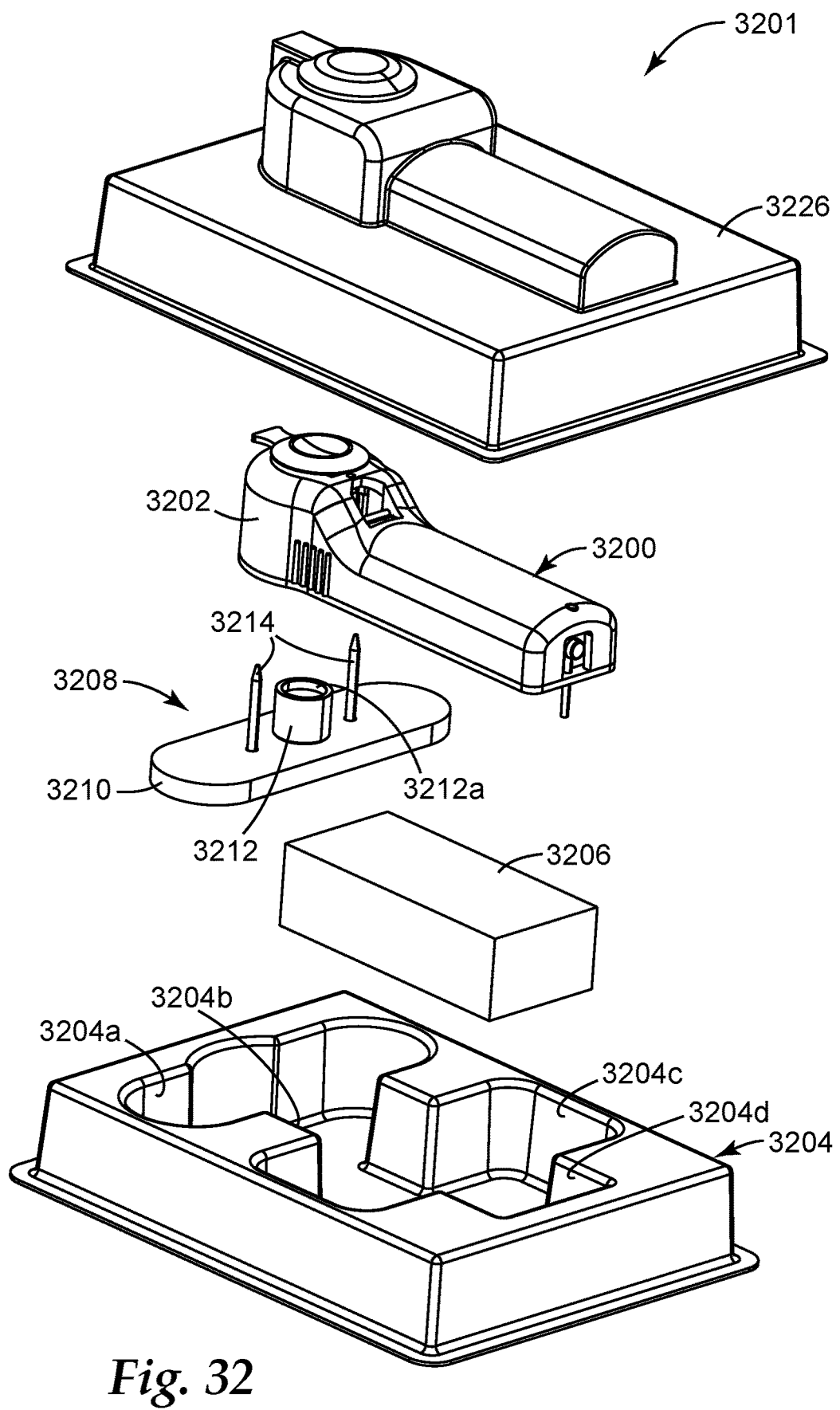
FIG. 32 is an exploded perspective view of a priming assembly.

Reference is made to FIG. 32 for illustrating one exemplary embodiment of controlled fluid release apparatus 3200 that is adapted to be used with priming system 3201. Priming system 3201 may include housing 3202 that has one or more recesses 3204a through 3204d. Housing 3202 may be made of any suitable material including, but not limited to, plastics, metal, and the like. A compressible and resilient block 3206 is provided that may fit within recesses 3204b through 3204d. Block 3206 allows a user to slightly compress it, such as when controlled fluid release apparatus 3200 is mounted thereon. Compression allows relative motion of controlled fluid release apparatus 3200 relative to stationary priming device 3208 located in recess 3204a. Block 3206 may be made of a suitable foam material having properties that allow it to be compressed and then resiliently return to its original condition. Examples, of such materials include an elastomeric plastic material, such as elastomeric urethane foam, and other similar materials.

Priming device 3208 includes elongated base 3210 that sits in housing 3202 and has an upstanding and generally cylindrically shaped priming tool 3212 extending upwardly. Also extending upwardly is a pair of guiding or aligning pins 3214 that limit displacement laterally of the controlled fluid release apparatus 3200. Pins 3214 may engage lateral sides of housing 3202. This serves to center or register controlled fluid release apparatus 3200 whereby priming tool 3212 may enter an opening (not shown), but corresponding to opening 115 in FIG. 3, to engage the microneedle applicator (not shown), in the controlled fluid release apparatus embodiment illustrated in FIGS. 1-13C. Priming tool 3212 has circular ridge 3212a that is adapted to engage peripheral rim portion 163a (FIG. 3) to not damage the microneedles.

In operation, a user mounts fluid release apparatus 3200 on compressible block 3206. A user pushes downwardly on controlled fluid release apparatus 3200. This compresses the block so that priming tool 3212 enters the opening and forces the applicator assembly upwardly against the first stored energy device until upper retaining member corresponding to 152 (FIG. 13A) is latched by a spring corresponding to resilient engaging device 150 (FIG. 13A). Upon effecting the priming condition, the user releases pressure and the resilient block returns to its unstressed condition for subsequent reuse.

The present description also envisions that the foregoing cradle may form a part of a package arrangement wherein the contents noted above may be shipped and stored. Package cover member 3226 may be provided that covers any one or all of controlled fluid release apparatus 3200, block 3206 and priming device 3208. The cradle, block, and the priming tool may be made of suitable materials to carry out the foregoing functions. Accordingly, a wide variety of materials may be used. Also, the recesses in the cradle may serve to allow a user to assemble and disassemble controlled fluid release apparatus 3200.

While the foregoing description provides one exemplary embodiment, the present disclosure envisions a wide variety of similar devices for pushing in on the microneedle assembly. As noted supra, alternatively or additionally, the present description envisions pulling on the microneedle assembly in order to prime it prior to use.

Figure 33:
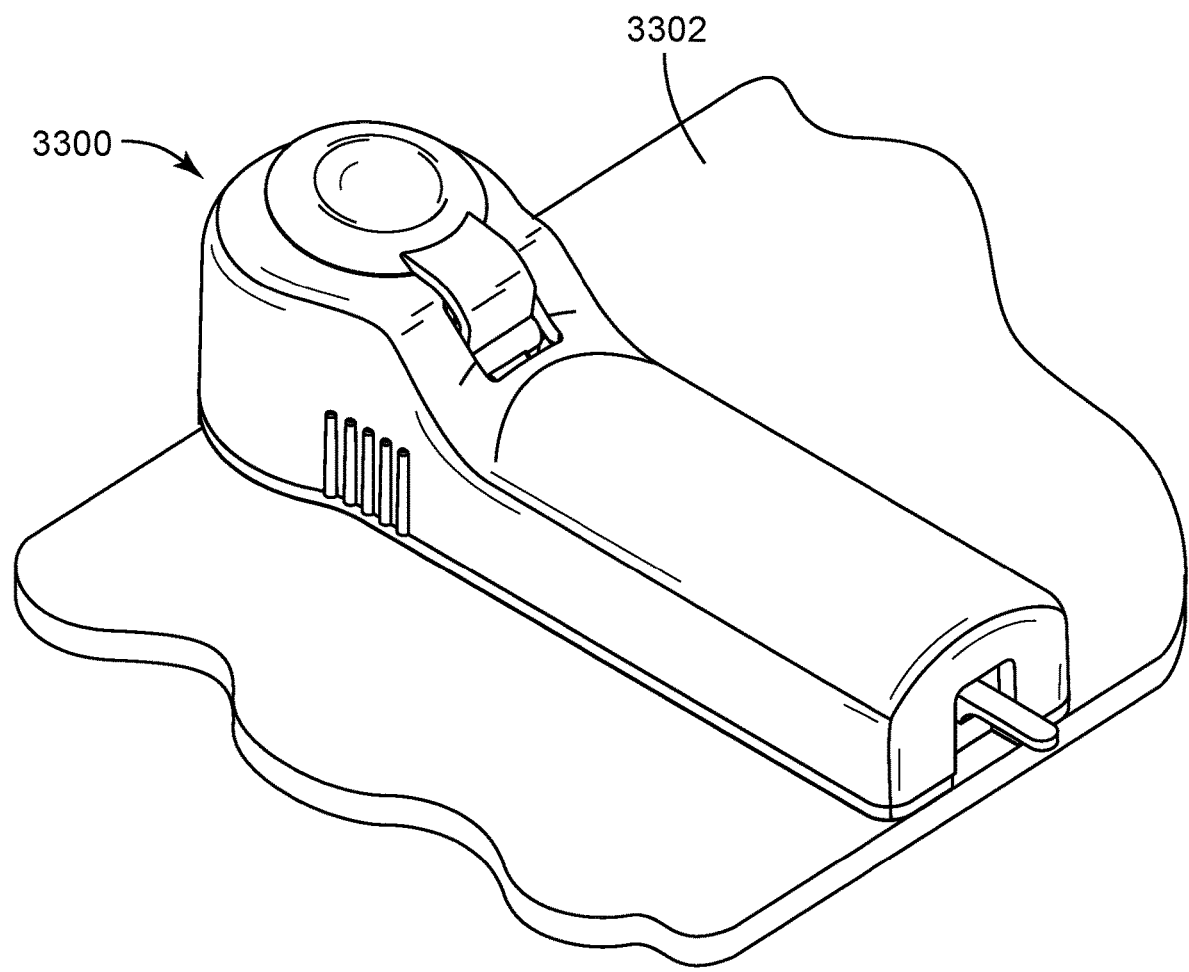
FIG. 33 is schematic view of the controlled fluid release apparatus of FIG. 1 in combination with a supporting device that is usable for supporting a portion of a body.

FIG. 33 is schematic view of controlled fluid release apparatus 3300 of FIG. 1 in combination with supporting device 3302 that is usable for supporting a portion of a body. While the illustrated embodiment discloses the foregoing embodiment, the present description is not so limited. Supporting device 3302 is adapted for supporting any body portion of patient. Controlled fluid release apparatus 3300 may include any of those described above and covered by the claims. Essentially, controlled fluid release apparatus 3300 is coupled to supporting device 3302. Controlled fluid release apparatus 3300 is connected to supporting device 3302 so that microneedles of a microneedle applicator assembly can penetrate a body portion when moving to their penetrating or released position, such as into a patient's skin while at the same time the supporting device supports the body portion. In this latter regard, supporting device 3302 may have an opening (not shown) in registry with an opening (not shown) of controlled fluid release apparatus 3300. In one exemplary embodiment, hollow microneedles are utilized. In other embodiments, needle applicators may be used for penetrating the skin or other body tissue.

Because of its compact nature and simple and reliable operation, controlled fluid release apparatus 3300 may be combined with the supporting devices of the kind described herein as well as others. While the present description envisions the use of controlled fluid release apparatus 3300, it will be appreciated that other similar types of fluid dispensing devices may be used in combination with the supporting devices. In many embodiments, a single actuation by a user can reliably infuse fluids. Controlled fluid release apparatus 3300 may have other constructions and operations besides those noted above. The present description envisions using fluid dispensing devices that may use hollow microneedles in combination with the supporting devices noted.

According to the present description supporting device 3302 may be from a group of supporting devices consisting of bandages, wound dressings, supporting garments, braces, and combinations thereof. The supporting devices may be otherwise attached, secured, or mounted on the body portion. The present description is not limited by the manner in which the supporting devices are attached. However, the supporting devices are attached to a patient, controlled fluid release apparatus 3300 is secured to the supporting devices so that in response to being actuated it can deliver the fluid to a patient without obstructing or otherwise interfering with microneedles penetrating.

It will be further understood that provisions are made for a method of treating a patient by infusing a fluid using an apparatus of the present invention.

The above embodiments have been described as being accomplished in particular sequences, it will be appreciated that such sequences of the operations may change and still remain within the scope of the present description. Also, other procedures may be added.

What is claimed is:

1. A method comprising:
    displacing a microneedle array in a direction perpendicular to a first major surface of an applicator, wherein the first major surface of the applicator comprises the microneedle array;
    opening an openable end of a drug cartridge;
    establishing fluid communication between the openable end and the microneedle array; and
    forcing fluid from the drug cartridge into the microneedle array through the openable end; wherein the drug cartridge, the applicator, and the microneedle array are components of an apparatus further comprising:
    a housing;
    the drug cartridge, the drug cartridge comprising a tubular member, a piston movable within the tubular member, and a fluid, wherein the drug cartridge has the openable end sealed by a septum and the piston is in sliding and sealing relationship with interior walls of the tubular member;

a manifold carrier fixedly attached to the microneedle array;

a pathway communicable between the openable end and the microneedle array, the pathway passing through the manifold carrier;

the housing supporting the applicator and the drug cartridge;

a first stored energy device actuatable for applying force to the applicator to accelerate the applicator in a direction generally normal to the first major surface; and a second stored energy device actuatable for automatically opening the openable end, such that the openable end and the pathway are in fluid communication, and wherein the second stored energy device includes a spring member that moves the piston relative to the housing so that the actuated second stored energy device forces the fluid through the openable end, the pathway, and the microneedle array; and wherein the housing includes an actuator for actuating the first and second stored energy devices.

2. The method of claim 1, wherein the microneedle array includes an array of hollow microneedles.

3. The method of claim 2, wherein the first stored energy device drives the array of hollow microneedles at a velocity ranging from between about 2 and 20 m/sec.

4. The method of claim 2, wherein the first stored energy device is supported on the applicator so that upon full release of the first stored energy device the first stored energy device decouples therefrom and is allowed to freely recoil and vibrate.

5. The method of claim 2, wherein the housing includes a portion thereof that restrains movement of the applicator, thereby minimizing recoil and retraction of the array of hollow microneedles upon full release of the first stored energy device.

6. The method of claim 2, wherein the first stored energy device continuously maintains positive pressure on the applicator upon full release of the first stored energy device.

7. The method of claim 2, wherein the hollow microneedles of the array of hollow microneedles have a length of from about 500 µm to about 1000 µm.

8. The method of claim 1, wherein the first stored energy device comprises a spring that has leg portions that straddle the drug cartridge, and a portion that contacts the applicator and the spring has a generally U-shape, and when unstressed lies adjacent the drug cartridge and generally parallel to a longitudinal axis of the drug cartridge.

9. The method of claim 1, wherein the drug cartridge is removably replaceable in the housing.

10. The method of claim 1, wherein the applicator includes a piercing needle operable to penetrate the septum.

11. The method of claim 1, wherein the second stored energy device automatically displaces the drug cartridge along an axis generally parallel to the first major surface.

12. The method of claim 1, wherein the second stored energy device includes first and second spring members, wherein the first spring member moves the drug cartridge to open the openable end, and the second spring member moves the piston to force the fluid from the drug cartridge when the openable end is opened.

13. The method of claim 1, wherein the applicator is releasably held in a primed condition by a releasable latching mechanism cooperating with the first stored energy device.

14. The method of claim 1, wherein the applicator comprises a releasable adhesive layer.

* * * * *